US009796995B2

(12) United States Patent
Sirois et al.

(10) Patent No.: US 9,796,995 B2
(45) Date of Patent: Oct. 24, 2017

(54) ENDOGENOUS AUTO-FLUORESCENT BIOLOGICAL MARKERS FOR ASSESSING A BIOLOGICAL PARAMETER OF A CELL

(71) Applicant: SOCPRA. SCIENCES ET GENIE S.E.C., Sherbrooke (CA)

(72) Inventors: Joël Sirois, Sherbrooke (CA); Emmanuel Bizier, Gatineau (CA); Guillaume Cardin-Bernier, Montreal (CA)

(*) Notice: Subject to any disclaimer, the term of this patent is extended or adjusted under 35 U.S.C. 154(b) by 0 days.

(21) Appl. No.: 14/926,350

(22) Filed: Oct. 29, 2015

(65) Prior Publication Data
US 2016/0130629 A1 May 12, 2016

Related U.S. Application Data

(63) Continuation of application No. 13/124,523, filed as application No. PCT/CA2009/001492 on Oct. 16, 2009, now abandoned.

(60) Provisional application No. 61/106,176, filed on Oct. 17, 2008, provisional application No. 61/106,181, filed on Oct. 17, 2008.

(51) Int. Cl.
*C12Q 1/02* (2006.01)
*G01N 21/64* (2006.01)
*G01N 33/58* (2006.01)

(52) U.S. Cl.
CPC ........... *C12Q 1/02* (2013.01); *G01N 21/6408* (2013.01); *G01N 21/6486* (2013.01); *G01N 33/582* (2013.01)

(58) Field of Classification Search
None
See application file for complete search history.

(56) References Cited

U.S. PATENT DOCUMENTS

2012/0028289 A1 2/2012 Sirois et al.

FOREIGN PATENT DOCUMENTS

WO 2010043021 4/2010
WO 2010043055 4/2010

OTHER PUBLICATIONS

Li et al. "Monitoring cell concentration and activity by multiple excitation fluorometry" Biotechnology Progress 7(1): 21-27, 1991.*
Park et al. "Cellular redox state predicts in vitro corneal endothelial cell proliferation capacity" Experimental Eye Research 83: 903-910, 2006.*
Byun et al., Elicitation of Sanguinarine Production in Two-Phase Cultures of Eschscholtzia californica, Journal of Fermentation and Bioengineering, vol. 73, No. 5, pp. 380-385 (1992).
Harrison, D.E.F., ang Chance, B., Fluometric Technique for Monitoring Changes in the Level of Reduced Nicotinamide Nucleotides in Continuous Cultures of Microorganisms, Applied Microbiology, vol. 19, No. 3, pp. 446-450 (1970).
Hisiger, S., and Jolicoeur, M., A multiwavelength fluorescence probe: Is one probe capable for on-line monitoring of recombinant protein production and biomass activity?, Journal of Biotechnology, vol. 117, pp. 325-336 (2005).
Hisiger, S., and Jolicoeur, M., Plant Cell Culture Monitoring Using an in Situ Multiwavelength Fluorescence Probe, Biotechnology Progress, vol. 21, No. 2, pp. 580-589 (2005).
Palmer et al., Autofluorescence Spectroscopy of Normal and Malignant Human Breast Cell Lines, Photochemistry and Photobiology, vol. 78, No. 5, pp. 462-469 (2003).
Surribas et al., Parallel factor analysis combined with PLS regression applied to the on-line monitoring of Pichia pastoris cultures, Anal. Bioanal. Chem., vol. 385, No. 7, pp. 1281-1288 (2006).
Tartakovsky et al., Application of Scanning Fluorometry for Monitoring of a Fermentation Process, Biotechnol. Prog., vol. 12, No. 1, pp. 126-131 (1996).
Vaidyanathan et al., Monitoring of Submerged Bioprocesses, Critical Reviews in Biotechnology, vol. 19, No. 4, pp. 277-316 (1999).
Boehl et al., Application of fluorescence spectroscopy for on-line bioprocess monitoring and control, Optical Methods for Industrial Processes, edited by Stuart Farquharson. Proceedings of SPIE, vol. 4201, pp. 50-57 (2001).
Chattopadhayay et al., Non-invasive Methods for Determination of Cellular Growth in Podophyllum hexandrum Suspension Cultures, Biotechnol. Bioprocess Eng. vol. 7, No. 6, pp. 331-334 (2002).
Haack et al., On-line cell mass monitoring of *Saccharomyces cervisiae* cultivations by multi-wavelength fluorescence, Journal of Biotechnology, vol. 114, No. 1-2, pp. 199-208 (2004).
Li, J., and Humphrey, A. E., Use of Fluorometry for Monitoring and Control of a Bioreactor, Biotechnology and Bioengineering, vol. 37, No. 11, pp. 1043-1049 (1991).
Lindemann et al., Two-dimensional fluorescence spectroscopy for application in biotechnology, SPIE Conference on Environmental Monitoring and Remediation Technologies, Boston, Massachusetts, edited by T. Vo-Dinh and R. L Spellicy, vol. 3534, pp. 83-90 (1998).
Marose et al., Two-dimensional Fluorescence Spectroscopy: A New Tool for On-Line Bioprocess Monitoring, Biotechnol. Prog. vol. 14, No. 1, pp. 63-74 (1998).
Skibsted et al., On-line bioprocess monitoring with a multi-wavelength fluorescence sensor using multivariate calibration, Journal of Biotechnology. vol. 88, No. 1, pp. 47-57 (2001).
Srivastava et al., Use of NADH fluorescence measurement for on-line biomass estimation and characterization of metabolic status in bioreactor cultivation fo plant cells for azadirachtin (a biopesticide) production, Process Biochemistry. vol. 43, pp. 1121-1123 (2008).

(Continued)

*Primary Examiner* — Emily Cordas
(74) *Attorney, Agent, or Firm* — Norton Rose Fulbright Canada LLP

(57) ABSTRACT

The present application related to the use of endogenous fluorescent biological markers to determine a parameter of a cell in a liquid Because the techniques provided herein provide accurate results in a relatively short amount of time, the methods described herein can be used to monitor and optimize cell culture online as well determine the presence of a cellular contamination in a cell suspension.

10 Claims, 8 Drawing Sheets

(56) References Cited

OTHER PUBLICATIONS

Wolfbeis et al., Chapter 3: The fluorescence of organic natural products, Molecular Luminescence Spectroscopy, Methods and Applications: Chemical Analysis, edited Schulmann, John Wilely and Sons, vol. 77 (Part 1): pp. 170-177, 1985.

Asali et al., Use of Nad(P)H-fluorescence in monitoring the response of starved cells of Catharanthus roseus in suspension to metabolic perturbations, Journal of Biotechnology, vol. 23, No. 1, pp. 83-93 (1992).

Farabegoli et al., Study on the use of NADH fluore3scence measurements for monitoring wasterwater treatment systems, Water Research, vol. 37, No. 11, pp. 2732-2738 (2003).

Horvath et al., In-Situ Fluorescence Cell Mass Measurements of *Saccharomyces cervisiae* Using Cellular Tryptophan, Biotechnology Progess, vol. 9, No. 6, pp. 666-670 (1993).

Kao, Staining Methods for Protoplasts and Cells, In: Wetter, L.R., Constabel, F. (eds.), PLant Tissue Culture Methods, Chapter 10, 2nd edition, National Research Council of Canada, Saskatoon, Canada, pp. 67-71 (1982).

Lindemann et al., 2-Dimensional fluorescence spectroscopy for on-line bioprocess monitoring, Sensors and Actuators B., vol. 51, Nos. 1-3, pp. 273-277 (1998).

Schalger, Status and Progess in On-Line Spectrometric Monitoring and Control of PLant Nutrient Solutions, Advances in Space Research, vol. 18, Nos. 4-5, pp. 113-124 (1996).

Scheper et al., On-Line Measurement of Cultrue Fluorescence for Process Monitoring and Control of Biotechnological Processes, Annals of the New Uork Academy of Sciences, vol. 506, pp. 431-445 (1987).

Siano, S.A., and Mutharasan, R., NADH and Flavin Fluorescence Responses of Starved Yeast Cultures to Substrate Additions, Biotechnollogy and Bioengineering, vol. 34, No. 5, pp. 660-670 (1989).

Sirois, Ph.D. thesis, École Polytechnique de Montréal (Dec. 2000) [Abstract].

\* cited by examiner

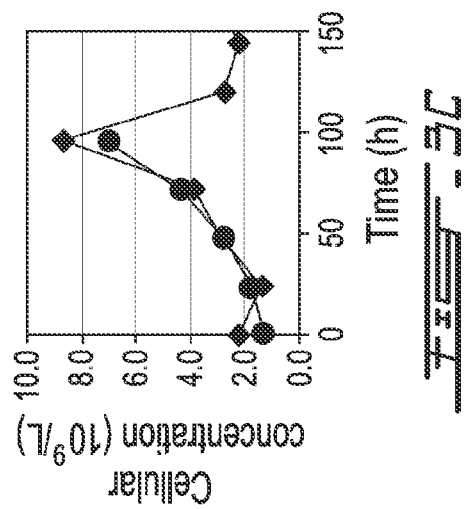
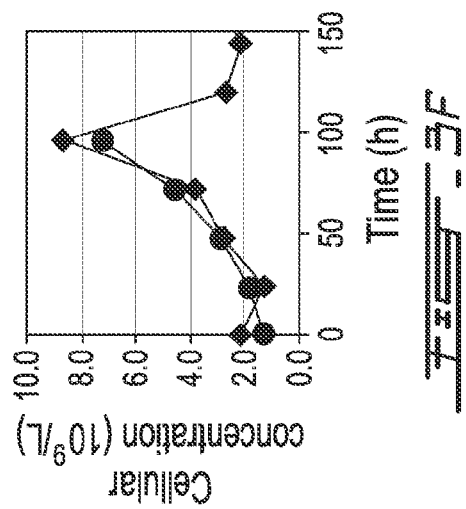
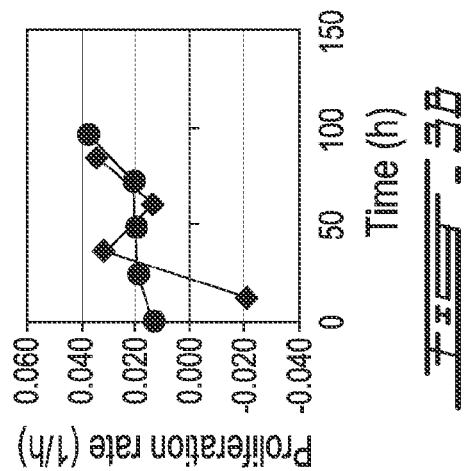
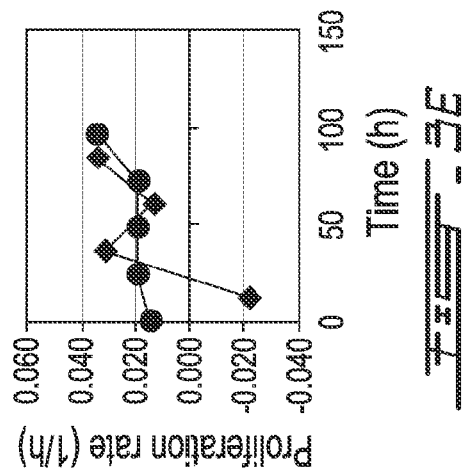
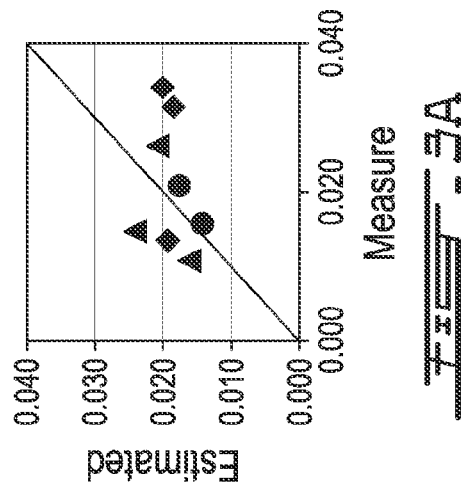
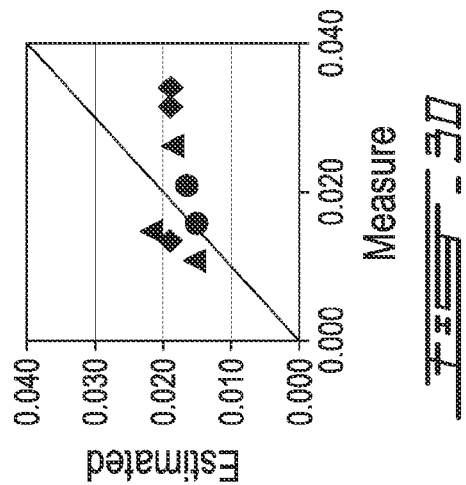

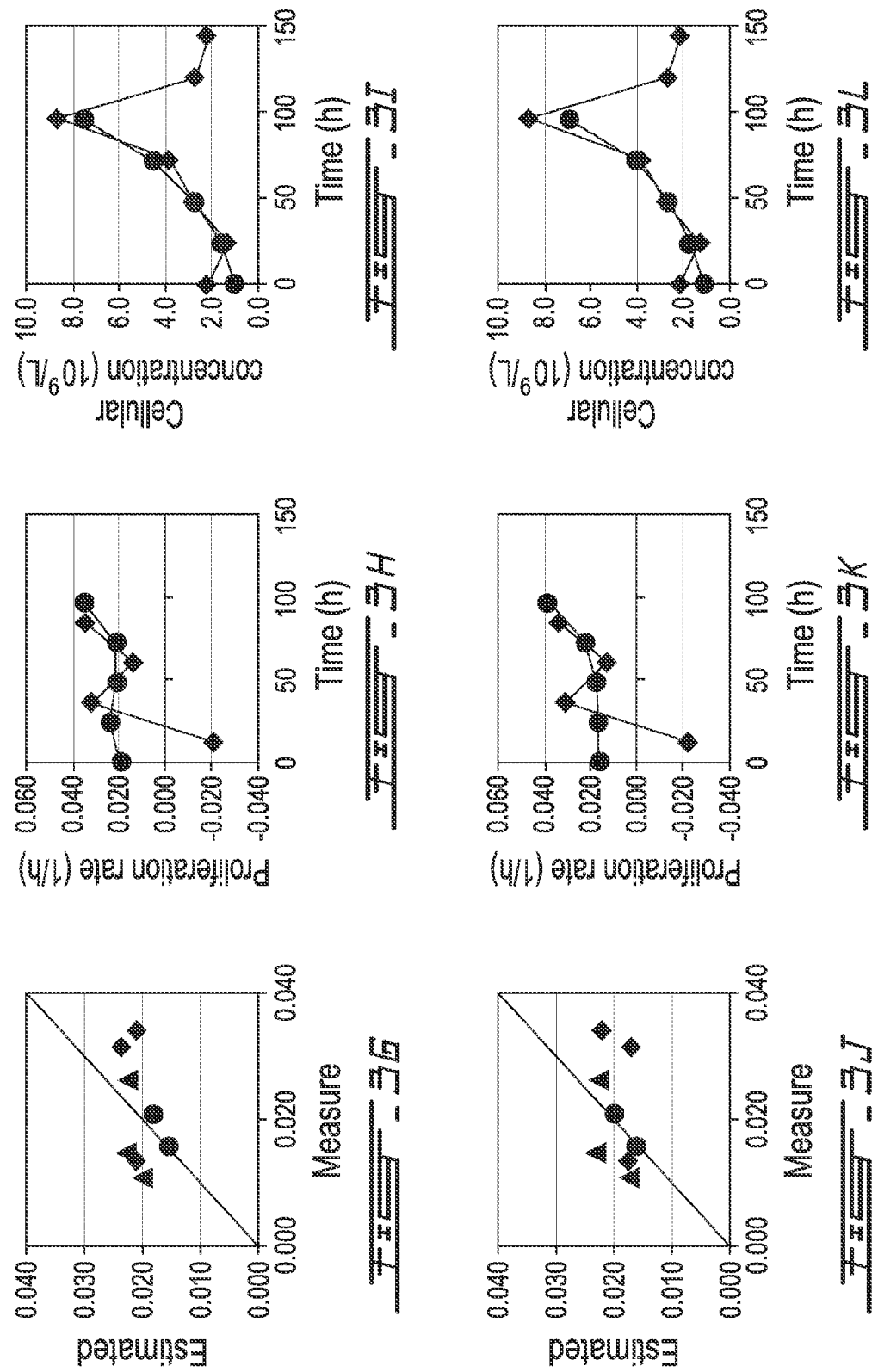

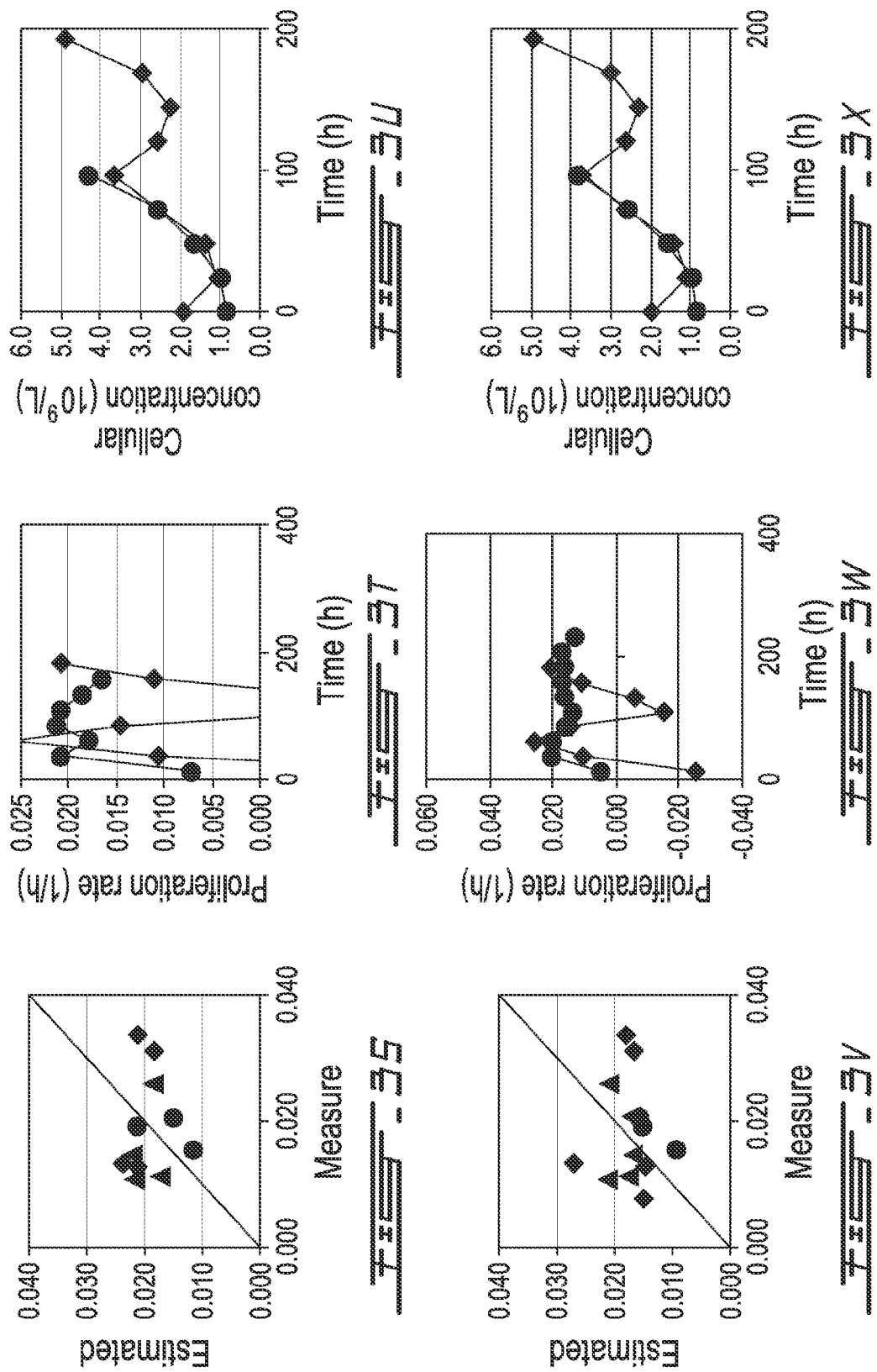

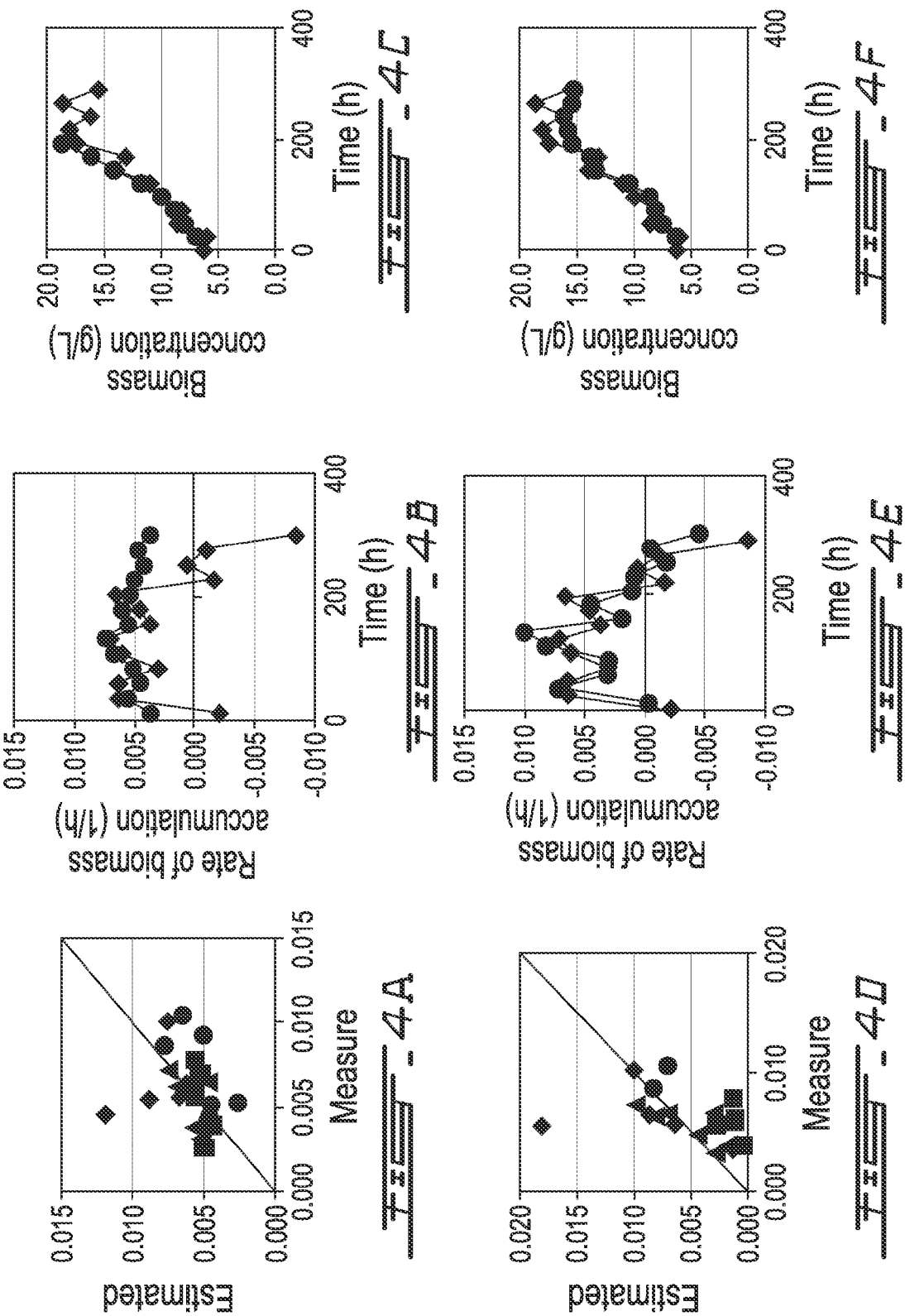

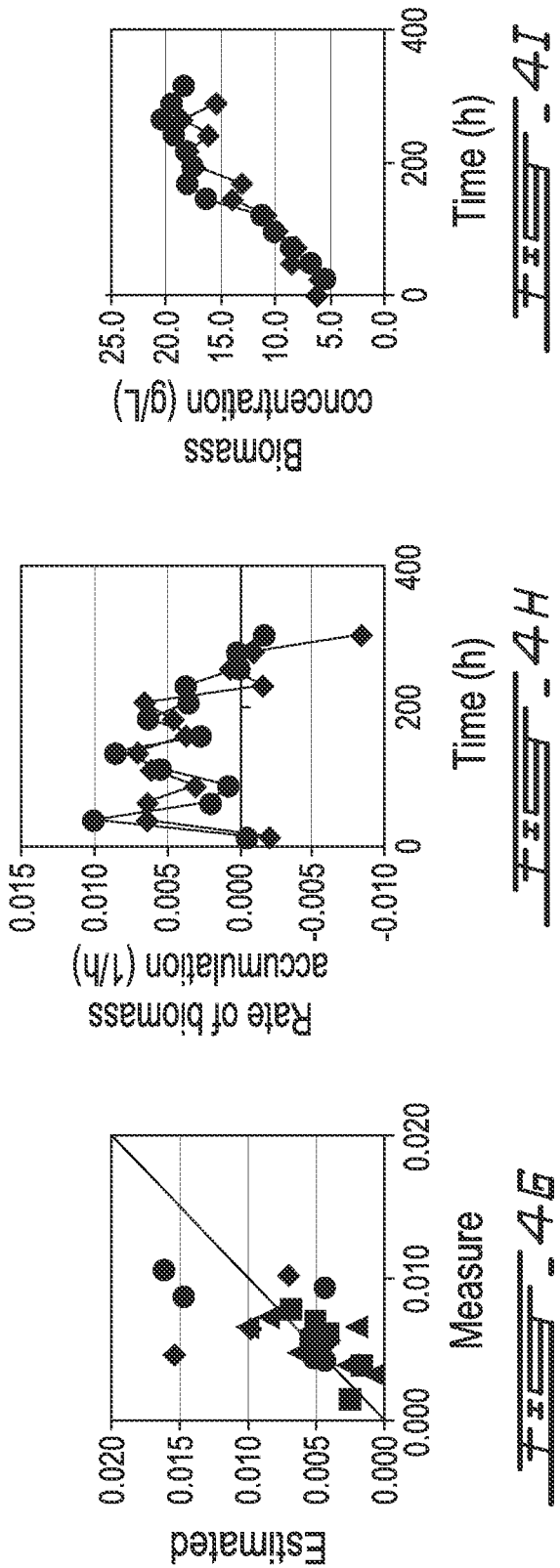

ENDOGENOUS AUTO-FLUORESCENT BIOLOGICAL MARKERS FOR ASSESSING A BIOLOGICAL PARAMETER OF A CELL

CROSS-REFERENCE TO RELATED APPLICATIONS

This application is a continuation application of U.S. application Ser. No. 13/124,523 which corresponds to a 371 application of PCT/CA2009/001492 filed on Oct. 16, 2009 and claims priority from U.S. provisional patent applications 61/106,176 and 61/106,181 both filed on Oct. 17, 2009. The related application are incorporated by reference in their entirety.

BACKGROUND

In order to control and optimize a cell culture, different parameters (growth curves, consumption/depletion of nutrients, production/accumulation of by products (which are usually toxic), determination of physiological state) must be determined at various stages. However, some parameters of a cell culture are very difficult to quantify because there is only a limited number of methods for measuring them during laboratory experimentation or industrial production. Usually, samples of the cell cultures are analyzed with conventional techniques (filtration, drying, cell counting, HPLC). These methods are generally lengthy and costly processes and cannot be performed in real time. Consequently, in industrial settings, cells are generally cultured using a pre-established recipe, based on a statistic indicator which can be indirectly linked to a specific cellular state. This strategy does not accommodate real time optimization of cell cultures and results in important economic loss.

Some methods currently known in the art enable the determination of the biomass concentration in real time: probes measuring a NADH signal through the determination of its auto-fluorescence in cell culture, turbidity (such as the ASD19-N™ of Optek Danulat) and capacitance (such as the BIOMASS MONITOR™ of Aber Instruments Ltd.). However, it is virtually impossible to determine in real time other important parameters of the cell culture such as cellular proliferation, physiological state, consumption of nutrients, production of a by-product, etc Even though the use of endogenous fluorescence to determine the status of a cell culture has proved to be difficult, some research teams have published their efforts toward the understanding of this subject. Hisiger et Jolicoeur (2005, Biotechnological Progress, 21, 580-589) found eight unknown fluorescent compounds in Eschscholtzia californica culture, as well as signal overlay of benzophenanthridic alkaloids and riboflavins. They also reported the relationship between NAD(P)H associated auto-fluorescence and cell activity in E. californica. They further reported the relation between NAD(P)H associated auto-fluorescence and biomass in C. roseus. Finally, they noted the relationship between NAD(P)H associated and riboflavin associated auto-fluorescence and growth rate in C. roseus. Applicant would like to note that the tryptophan and tryptamine signals were inverted in their studies. Applicant would also like to point out that the same indicator (NAD(P)H) was correlated to two physiological variables which are linearly independent. This conclusion was supported by only one reading which can lead to a erroneous interpretation of the real and reproducible correlations.

Hisiger and Jolicoeur (2005, Journal of Biotechnology, 117, 325-336) then reported the relationship between NAD (P)H, riboflavin and tryptophan-associated auto-fluorescence and biomass concentration in P. pastoris. They also suggested the relationship between riboflavin associated auto-fluorescence and biomass concentration in the NSO cell line. Surprisingly, even if riboflavin and tryptophan are not bio-synthesized by mammal cells, Hisiger and Jolicoeur pretend that it is <<possible>> to correlate the biomass concentration and the riboflavin-associated auto-fluorescence. However, Hisiger and Jolicoeur also add that "[ . . . ] the presence of some unidentified fluorescence signals that are overlapping the ones of interest [ . . . ] are limiting the applicability and the reliability of this type of probe".

Schalger et al. (1996, Advanced Space Research, 18, 113-124) developed algorithms to track microbial population evolution of Pseudomonas aeroginosa by auto-fluorescence. Schalger et al. reported estimation errors up to 42.9%.

Asali et al. (1992, Biotechnology, 23, 83-94) reported the relationship between NAD(P)H associated fluorescence and biomass concentration in C. roseus.

Farabegoli et al. (2003, Water Research, 37, 2732-2738) reported the relation between NAD(P)H associated auto-fluorescence and biomass concentration in active mud.

A relationship between NAD(P)H-associated auto-fluorescence and biomass concentration in C. botanica was also identified by Harrison et Chance (1970, Applied microbiology, 19, 446-450).

Horvath et al. (1993, Biotechnology progress, 9, 666-670) reported a relationship between tryptophan-associated auto-fluorescence and biomass concentration in S. cerevisae.

Li et Humphrey (1991, Biotechnology and Bioengineering, 37, 1043-1049) reported the relationship between NAD (P)H, riboflavin, tryptophan and pyridoxine associated auto-fluorescence and biomass concentration in C. utilis. A relationship between tryptophan-associated auto-fluorescence and biomass concentration in S. cerevisae was also reported by this group.

Also in S. cerevisae, Lindemann et al. (1998, Sensors and actuators B, 51, 273-277) reported a relationship between riboflavin-associated auto-fluorescence and biomass concentration.

Palmer et al. (2003, Photochemistry and photobiology, 78, 5, 462-469) published the relationship between tryptophan-associated auto-fluoescence and cellular concentration in human mammal cells. Their correlation was not used to monitor cell culture, but to discriminate between malignant and normal phenotypes in different cell lines.

Scheper et al. (1987, Annals New York Academy of Sciences, 506, 431-445) reported the relationship between NAD(P)H-associated auto-fluorescence and cellular activity in various organisms.

Siano et Mutharasan (1989, Biotechnology and Bioengineering, 34, 660-670) published the relationship between NAD(P)H-associated auto-fluorescence and cellular activity in S. cerevisae.

As shown herein, some endogenous auto-fluorescent markers have been suggested to be correlated with biomass concentration in some cell culture. However, information regarding to biomass concentration/accumulation provides only partial information about the cell culture. For example, it does not provide information about the metabolic behavior of the cells in culture (ex.: cell proliferation, nutriments consummation and use, metabolic activity, etc.).

In light of the above, it would be highly desirable to be provided with appropriate markers that are accurate representatives of one or several parameters of a cell culture. These markers should be rapidly measured in order to provide real time or quasi real time information on the status of the cell culture or to detect a cellular contamination. These markers should also be able to represent different culture parameters in order to provide very important information on the status of the cell culture.

BRIEF SUMMARY

The present application relates to endogenous auto-fluorescent biological markers associated with a biological parameter of a cell as well as their use in the determination of such biological parameter.

According to one aspect, the present application provides a method of determining a biological parameter of a cell in a liquid. The method broadly comprises a) quantifying a fluorescent signal associated with an endogenous auto-fluorescent biological marker to obtain a fluorescent value; and b) estimating the biological parameter of the cell based on the fluorescent value obtained in step a). In an embodiment, the fluorescent signal of the endogenous auto-fluorescent biological marker is quantified at a specific excitation wavelength and a specific emission wavelength. In another embodiment, the fluorescent signal of the endogenous auto-fluorescent biological marker clearly distinguishes from or does not overlap with another detected fluorescent signal.

In an embodiment, the fluorescent signal of the endogenous auto-fluorescent biological marker results from the auto-fluorescence of a single biological molecule or a combination of more than one biological molecule.

In another embodiment, the cell is in a liquid medium or in suspension. In a further embodiment, the liquid is a culture medium or a neutral liquid which does not interfere with the fluorescence reading.

In yet another embodiment, the liquid containing the cell is filtered prior to quantification step to generate a filtrate and a retentate. In an embodiment, the filtrate is submitted to quantification step. In another embodiment, the retentate is submitted to the quantification and, in a further embodiment, the retentate is suspended in a neutral liquid prior to being submitted to the quantification step. In still another embodiment, both the filtrate and the retentate are submitted to the quantification step.

In still another embodiment, the biological parameter that is determined by the method is the biomass concentration (g/L). In an embodiment, the biomass concentration is a dry biomass concentration. In still another embodiment, the endogenous auto-fluorescent biological marker is associated with tryptamine and, in a further embodiment, the specific excitation wavelength of this endogenous auto-fluorescent biological marker is between about 220 and 240 nm and/or the specific emission wavelength of this endogenous auto-fluorescent biological marker is between about 342 and 362 nm. In yet another embodiment, the endogenous auto-fluorescent biological marker is associated with FAD and, in a further embodiment, the specific excitation wavelength of this endogenous auto-fluorescent biological marker is between about 421 and 441 nm and/or the specific emission wavelength of this endogenous auto-fluorescent biological marker is between about 525 and 545 nm. In still a further embodiment, the endogenous auto-fluorescent biological marker is associated with a combination of riboflavin and FAD and, in still a further embodiment, the specific excitation wavelength of this endogenous auto-fluorescent biological marker is between about 442 and 462 nm and/or the specific emission wavelength of this endogenous auto-fluorescent biological marker is between about 522 and 542 nm.

In a further embodiment, the biological parameter that is determined by the method is cellular concentration. In another embodiment, the cellular concentration is indicative of a cellular contamination. In a further embodiment, the endogenous auto-fluorescent biological marker is associated with riboflavin and, in still a further embodiment, the specific excitation wavelength of this endogenous auto-fluorescent biological marker is between about 358 and 378 nm and/or the specific emission wavelength of this endogenous auto-fluorescent biological marker is between about 516 and 536 nm. In another embodiment, the endogenous auto-fluorescent biological marker is associated with FAD and, in still a further embodiment, the specific excitation wavelength of this endogenous auto-fluorescent biological marker is between about 358 and 378 nm and/or the specific emission wavelength of the endogenous auto-fluorescent biological marker is between about 522 and 542 nm.

In still another embodiment, the biological parameter that is determined by this method is a rate of cellular proliferation ($h^{-1}$). In an embodiment, the estimation of the biological parameter is corrected by shifting the signal over time (by a cellular cycle or a sampling time for example). In an embodiment, the endogenous auto-fluorescent biological marker is associated with pyroxidin and, in still a further embodiment, the specific excitation wavelength of this endogenous auto-fluorescent biological marker is between about 253 and 397 nm and/or the specific emission wavelength of this endogenous auto-fluorescent biological marker is between about 387 and 407 nm. In another embodiment, the endogenous auto-fluorescent biological marker is associated with NAD(P)H and, in still a further embodiment, the specific excitation wavelength of this endogenous auto-fluorescent biological marker is between about 265 and 285 nm and/or the specific emission wavelength of this endogenous auto-fluorescent biological marker is between about 438 and 458 nm. In a further embodiment, the endogenous auto-fluorescent biological marker is associated with NAD(P)H and, in still a further embodiment, the specific excitation wavelength of this endogenous auto-fluorescent biological marker is between about 340 and 360 nm and/or the specific emission wavelength of this endogenous auto-fluorescent biological marker is between about 435 and 455 nm. In still a further embodiment, the endogenous auto-fluorescent biological marker is associated with riboflavin and, in still another embodiment, the specific excitation wavelength of this endogenous auto-fluorescent biological marker is between about 265 and 285 nm and/or the specific emission wavelength of this endogenous auto-fluorescent biological marker is between about 520 and 540 nm. In still a further embodiment, the endogenous auto-fluorescent biological marker is associated with ATP and, in still another embodiment, the specific excitation wavelength of this endogenous auto-fluorescent biological marker is between about 290 and 310 nm and/or the specific emission wavelength of this endogenous auto-fluorescent biological marker is between about 390 and 410 nm. In another embodiment, the endogenous auto-fluorescent biological marker is associated with FAD and, in still a further embodiment, the specific excitation wavelength of this endogenous auto-fluorescent biological marker is between about 421 and 441 nm and/or the specific emission wavelength of this endogenous auto-fluorescent biological marker is between about 525 and 545 nm. In another embodiment, the endogenous auto-fluorescent biological marker is a associated with a combination of riboflavin and FAD and, in still a further embodiment, the specific excitation wavelength of this endogenous auto-fluorescent biological marker is between about 442 and 462 nm and/or the specific emission wavelength of this endogenous auto-fluorescent biological marker is between about 522 and 542 nm.

In a further embodiment, the biological parameter is a rate of biomass accumulation ($h^{-1}$). In an embodiment, the endogenous auto-fluorescent biological marker is associated with NAD(P)H and, in still a further embodiment, the specific excitation wavelength of this endogenous auto-fluorescent biological marker is between about 265 and 285 nm and/or the specific emission wavelength of this endogenous auto-fluorescent biological marker is between about 438 and 458 nm. In another embodiment, the endogenous auto-fluorescent biological marker is associated with pyridoxine and, still in a further embodiment, the specific excitation wavelength of this endogenous auto-fluorescent biological marker is between about 313 and 333 nm and/or the specific emission wavelength of the endogenous auto-fluorescent biological marker is between about 384 and 404 nm. In yet another embodiment, the endogenous auto-fluorescent biological marker is associated with sanguinarine and, still in a further embodiment, the specific excitation wavelength of this endogenous auto-fluorescent biological marker is between about 346 and 366 nm and/or the specific emission wavelength of this endogenous auto-fluorescent biological marker is between about 588 and 608 nm.

In still a further embodiment, there is provided a method of determining at least one a biological parameter of a cell in a liquid. Broadly, the method comprises a) quantifying a fluorescent signal associated with at least one endogenous auto-fluorescent biological marker to obtain a fluorescent value; and b) estimating the biological parameter of the cell based on the fluorescent value obtained in step a). In an embodiment, the fluorescent signal of the endogenous auto-fluorescent biological marker is quantified at a specific excitation wavelength and a specific emission wavelength. In another embodiment, the at least one biological parameter is biomass concentration, cellular concentration, a rate of cellular proliferation and/or a rate of biomass accumulation. In a further embodiment, the at least one endogenous auto-fluorescent biological markers is associated with: i) biomass concentration and with tryptamine, FAD and/or a combination of riboflavin and FAD; ii) cellular concentration and with riboflavin and/or FAD; iii) a rate of cellular proliferation and pyroxidin, NAD(P)H, riboflavin, ATP, FAD and/or a combination of riboflavin and FAD; and/or iv) a rate of biomass accumulation and NAD(P)H, pyroxidine and sanguinarine. In an embodiment, more than one biological parameter is determined by this method. In another embodiment, more than one endogenous biological auto-fluorescent marker is used in the determination of one biological parameter.

BRIEF DESCRIPTION OF THE DRAWINGS

FIG. 4A to 4I illustrate the estimated rate of biomass accumulation ($h^{-1}$) and the estimated biomass concentration (g/L) based on the fluorescence value obtained for three different markers and the offline measure of the same parameters. In A, D and G the estimated rate of biomass accumulation based on the fluorescence value of different markers is plotted against the offline measure of the rate of biomass accumulation. The results of three different independent experiment ($\diamond$ experiment 1, $\circ$ experiment 2, $\Delta$ experiment 3) are shown. In B, E, and H representative results of a single experiment that determined the rate of biomass accumulation as a function of the length of the culture (in hours) is shown both for the estimated rate of biomass growth based on the fluorescence value of different markers ($\circ$) and the offline measures ($\diamond$). In C, F and I representative results of a single experiment that determined the biomass concentration as a function of the length of the culture (in hours) is shown both for the estimated biomass concentration based on the fluorescence value of different markers ($\circ$) and the offline measures ($\diamond$). Results obtained with a NAD(P)H associated fluorescent signal ($\lambda_{excitation}$ 275 nm, $\lambda_{emission}$ 448 nm) as a marker from the retentate are shown in A, B and C. Results obtained with a pyridoxine associated fluorescent signal ($\lambda_{excitation}$ 323 nm, $\lambda_{emission}$ 394 nm) as a marker from the retentate are shown in D, E and F. Results obtained with a sanguinarine associated fluorescent signal ($\lambda_{excitation}$ 356 nm, $\lambda_{emission}$ 598 nm) as a marker from the retentate are shown in G, H and I.

DETAILED DESCRIPTION

Figure 1A:
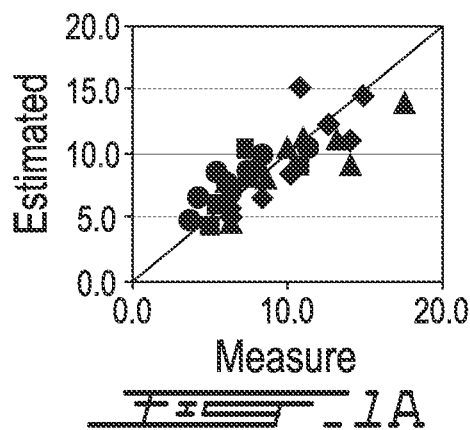
FIG. 1A to 1F illustrate the estimated biomass concentration (g/L) based on the fluorescence value obtained for three different markers and the offline measure of the biomass concentration obtained with traditional techniques. In A, C and E the estimated biomass concentration based on the fluorescence value of different markers is plotted against the offline measure of the biomass concentration. The results of four different independent experiments ($\diamond$ experiment 1, $\circ$ experiment 2, $\Delta$ experiment 3, $\square$ experiment 4) are shown. In B, D and F, representative results of a single experiment that determined the biomass concentration in function of the length of the culture (in hours) is shown for both the estimated biomass concentration based on the fluorescence value of different markers ($\circ$) and the offline measures ($\diamond$). Results obtained with a tryptamine associated fluorescent signal ($\lambda_{excitation}$ 230 nm, $\lambda_{emission}$ 352 nm) as a marker are shown in A and B. Results obtained with a FAD associated fluorescent signal ($\lambda_{excitation}$ 431 nm, $\lambda_{emission}$ 535 nm) as a marker are shown in C and D. Results obtained with a riboflavin/FAD associated signal ($\lambda_{excitation}$ 452 nm, $\lambda_{emission}$ 532 nm) as a marker are shown in E and F.

In accordance with the present invention, there is provided endogenous auto-fluorescent biological markers and their use in the determination of a biological parameter of cell in a liquid. The endogenous biological markers can be also be used in the optimization of various parameters of a cell culture as well as for the determination of a cellular contaminant in a liquid.

As indicated above, many groups have tried to tie a specific fluorescent signal with a parameter of cell culture, in various systems. However, these groups have failed to provide a fluorescent signal that is biologically relevant and that is soundly associated with a biological parameter of a cell culture.

In the present application, the endogenous auto-fluorescent biological markers presented show an excellent correlation with one or more biological parameter of a cell in a liquid. As such, the determination of the presence/level of these endogenous auto-fluorescent biological markers can be used to predict or estimate a biological parameter of the cell.

As contemplated herewith, the present invention relates to "endogenous auto-fluorescent biological markers" which refer to a marker that is self-fluorescent, that is associated with the metabolic activity of a cell, that is correlated with a biological parameter of the cell and that clearly distinguishes from other auto-fluorescent sources (e.g. does not overlap with other non- or less-specific fluorescent signals). The markers described herein are auto-fluorescent, e.g. they specifically emit light (e.g. they fluoresce) when they are excited at a specific wavelength without the need of adding a substrate or a fluorogenic molecule The markers described herein are also associated with the metabolic activity of a cell because they are either produced or consumed by a cell during its life cycle. In other words, these markers are natively consumed or produced by the cells during their life cycle and do not need to be added to the cell or its environment to be detected. The markers described herein are also correlated to a biological parameter of the cell, a parameter that is modulated during the life cycle of a cell or a culture of cells. Such biological parameters include, but are not limited to biomass accumulation and its associated rate, cellular concentration, rate of cellular proliferation, etc.

The endogenous auto-fluorescent biological marker is not a molecule per se (or a combination thereof) but the fluorescent signal associated with the molecule and obtained at a specific excitation/emission wavelength couple. As used herein, the expression "fluorescent signal" and "fluorescent value" are used interchangeably and refer to a measure of fluorescence. The specific excitation/emission wavelength couple of the endogenous auto-fluorescent biological marker can be associated with a single molecule or a combination of molecules associated with the cell. As known in the art, some molecules associated with the metabolic activity of the cell intrinsically emit fluorescence when excited at the appropriate wavelength, they are said to be auto-fluorescent. A single auto-fluorescent molecule can have one or more than one excitation/emission wavelength couples. In addition, more than one molecule can have the same or relatively similar excitation/emission wavelength couples. Consequently, the endogenous auto-fluorescent biological marker is a fluorescent signal obtained at a specific excitation/emission wavelength couple that is tied to the metabolic activity of the cell because the fluorescent signal is derived from a molecule (or a combination thereof) that is associated with cellular metabolism.

In order to determine which endogenous auto-fluorescent biological marker should be selected to estimate a biological parameter, cultures of various cells have been performed and fluorescent readings have been obtained at excitation/emission wavelength couples specific for various auto-fluorescent molecules (and combinations thereof) associated with cellular metabolism. A mathematical correlation was then performed to determine if a specific endogenous auto-fluorescent biological marker is associated with a specific biological parameter. As used herein, the endogenous auto-fluorescent biological marker is "specific for a biological parameter" because it is indicative of the modulation of a biological parameter or a cell or a culture of cells. In an embodiment, a marker cannot be used for estimating two or more parameter which are linearly independent.

Two types of markers have been discovered by this methodology. The first type of markers consists of endogenous auto-fluorescent biological markers associated with a single molecule and that have a fluorescent signal which clearly distinguishes from other unrelated auto-fluorescent signals. The second type of markers consists of a combination of at least two molecules whose respective fluorescent signal cannot be distinguished from one another but, as a whole, clearly distinguish from other unrelated auto-fluorescent signals.

The various markers described herein are excited at a specific wavelength are emit at a specific wavelength. Examples of the excitation/emission couples of various endogenous biological markers are set forth in Table 1. The excitation/emission can vary depending on many factors, such as the methodology used to provide and quantify the light signals, the distance between two endogenous biological auto-fluorescent molecules, the presence of a fluorescent masking agent non-specific auto-fluorescence from the liquid containing the cell, etc. As such, even though very specific excitation/emission couples are used herein, they may, depending on the application, depart from ±20 nm, ±10 nm, ±5 nm or ±2 nm from the specific excitation/emission couples set forth herein.

One particular advantage of the endogenous auto-fluorescent biological markers described herein is they are derived from the auto-fluorescence of molecules endogenously produced (e.g. native) or consumed by the cells of the culture. As such, there is no need to add a fluorescent or fluorogenic compound to the sample of cells, during their culture, to provide valuable information on the state of the cell (or cell culture). There is also no need to genetically modify the cells to enable them to produce a fluorescent of fluorogenic compound during culture.

Another advantage is that these markers can be used to develop online reading of the cell culture (with a probe for example) that is added directly in the cell culture vessel, thereby eliminating the need of sampling the culture to generate information about its status. As used herein, the term "online" refers to a process or method that can be performed without sampling the cell culture. Online methods or processes generally use a probe that is adapted in a culture vessel to contact directly the cell culture. Online methods and processes are advantageous because they generate rapidly information relating to the cell culture without the need for sampling.

A further advantage of the markers presented herewith is that they are each associated with a specific biological parameters and provide a relatively precise correlation with the biological parameter. In addition, the various markers presented herewith can be used independently or in combination to provide information about a single or various biological parameters of the cell suspension.

A yet another advantage is that, since the markers described herein are intrinsically associated with the presence of a cell (and implicitly metabolic activity), the markers can also be used to detect a cellular contamination in a composition. In order to achieve this goal, the fluorescent signal associated with the marker is determined in the composition and compared to a threshold level, associated with a tolerated level of cellular contamination. In some composition, no cellular contamination will be tolerated. In other composition, a certain level of cellular contamination is tolerated. If the signal obtained is higher than the predetermined threshold, then the composition is considered contaminated and is discarded or treated to lower the level of cellular contamination.

Yet another advantage of the markers described herein is that they seem to be associated with the same biological marker, independently of the type of cell that is being analysed. For example, a tryptamine-associated endogenous auto-fluorescent marker is associated with biomass accumulation in plant cells, yeast cells, microalgae, bacteria and animal cells. The markers seem thus appropriate to detect a biological parameter in any kind or type of cells.

The endogenous auto-fluorescent biological markers can be associated with the cell directly (intracellularly, embedded or associated with the membrane for example), can be consumed by the cell (e.g. disappear from the liquid) or can be released by the cell in the liquid. As such, and even though sampling is not necessary to perform the method presented herewith, it might be useful to take a sample from the liquid containing the cell(s) and dissociate the cell from the liquid prior to the determination of the presence of the endogeneous auto-fluorescent biological marker. This step can be achieved, for example, by filtering or centrifuging a cellular liquid suspension and, optionally resuspending the cells (centrifuged or filtered out) in another liquid medium. This other liquid medium could be, for example, a neutral liquid, neutral in a sense that it will not interfere with the fluorescent excitation/emission or reading of the endogenous auto-fluorescent biological marker. This further step can generate data with respect to the location of the endogenous auto-fluorescent biological marker and consequently provide additional information concerning the biological parameter of the cell. This additional step can also eliminate the original liquid suspension itself which, in certain circumstance, can auto-fluoresce and mask the fluorescent signal associate with the endogenous auto-fluorescent biological markers.

The endogenous auto-fluorescent biological marker associate with a cell is preferably detected in a liquid. As used herein, the term "a cell in liquid" refers to a cell that is, has been or will be placed in a liquid (e.g. aqueous) medium. The cell may optionally be cultured/propagated in that liquid medium. The cell in liquid can be an ongoing cell culture, a sample thereof or a derivative thereof. Derivatives of the cell culture include, but are not limited to, the cellular pellet, the cellular supernatant, the cellular filtrate, the cellular retentate and the cellular extract.

As indicated above, the markers can be used in methods performed online with a probe adapted to be used in a culture vessel as well as offline by sampling the culture at various intervals. When a sample is analyzed offline, the sample that is retrieved from the cell culture can be further processed before fluorescence quantification. For example, the cells can be lysed, enzymatically treated, centrifuged or filtered prior to fluorescence quantification. However, to identify the source of the auto-fluorescence, the sample can be filtered and the fluorescence quantification can be performed on the retentate that has been resuspended in an appropriate buffer (e.g. cells resuspended, for example, in a saline solution) and the filtrate (e.g. cell free culture medium). In this particular embodiment, the fluorescence obtained for the retentate will generate information about the fluorescence associated with the cells, whereas the fluorescence associated with the medium will generate information about the fluorescence associated with the medium (such as nutrients consumed by the cells of the culture or by-products of the cells of the culture).

A further advantage of the endogenous biological markers is that they can be used on static (batch) culture, fed-batch culture, continuous or perfused culture. The term "continuous culture" refers to the growth of cells in culture medium in a culture chamber, whereby fresh medium or elements thereof is added while suspension is partially removed. Medium adding rate and suspension removal rate are generally the same so as to keep the culture volume approximately constant. "Perfused culture" refers to the growth of cells in culture medium in a culture chamber, whereby fresh medium or elements thereof are added while culture medium is partially removed whereas cells are retained in the culture chamber. Fresh medium adding rate and culture medium removal rate are generally the same so as to keep the culture volume approximately constant. On the contrary, the term "static culture" refers to the growth of cells for a definite period of time where the cells and medium are both recuperated at the end of the incubation and where no additional medium is added during the culture and no suspension is removed. Further, the term "fed-batch culture" refers to an hybrid of the previous two culture methods, where, during the culture, some fresh medium or elements thereof is added to the culture. However, in fed-batch culture, no suspension is removed.

The fluorescence associated with the endogenous auto-fluorescent biological marker can be quantified by various means in the art. Fluorescence in several wavelengths can be detected by an array detector, to detect compounds from HPLC flow. Also, thin layer chromatography plates and microscopy can also be used to visualize the endogenous biological marker. Ideally, the fluorescence of a sample is determined rapidly and accurately with a spectrophotometer. The determination of the fluorescence does provide a certain transient transformation of the cellular suspension. The cellular suspension (or sample thereof) is submitted to a transient excitation wavelength and, if the endogenous auto-fluorescent marker is present in the suspension or its sample, a transient emission of light at a specific wavelength will be generated and can be quantified. As such, even the method itself is not necessarily destructive it does provide a transient transformation of the cellular suspension or sample thereof.

As it is known in the art, cells are important biocatalysts that can be used for the production of a wide range of bioactive compounds including pharmaceuticals (antibiotics, antibodies, codeine, scopalamine, vincristine, ajmalicine, and digoxin); flavors and fragrances (strawberry, vanilla, rose, and lemon); sweeteners (thaumatin and monellin); food colors (anthocyanin and saffron), food additives and pesticides (thiophenes, azadirachtins, nicotine). Important markets exist for these bioactive compounds, which are normally obtained by extraction from intact biomass. In view of the growing world population, increasing anthropogenic activities and rapidly eroding natural ecosystems, the natural habitats for a large number of species are rapidly diminishing leading to the extinction of many valuable species.

The endogenous auto-fluorescent biological markers presented herein can be used to monitor, optimize and/or control cultures of a variety of cells. The endogenous auto-fluorescent biological markers presented herein can be quantified in a liquid medium. As such, the cells that are being monitored are preferably be cultured in vitro. However, methods can be modified, according to the knowledge of those skilled in the art, to accommodate the monitoring of cells that are not cultured in vitro. In these instances, it is favorable to generate a sample of cells or a cell extract in liquid from cells that are not grown in vitro.

As shown herein, the cells that can be monitored with the endogenous auto-fluorescent biological markers presented herein are not limited to a particular type or species. Cells from all origins can be monitored by the endogenous auto-fluorescent biological markers presented herein. The cells may be derived from a single cell type as well as mixture thereof. These cells include prokaryotic cells and eukaryotic cells.

Even though the methods described herein do not rely on the use of genetic engineering to produce a fluorescent signal, cells that have been genetically modified or chemically mutated can also be used. The methods provided herewith will enable the determination of various parameters associated with their culture and will enable the optimization of their culture.

In an embodiment, the cells are prokaryotic in nature. Prokaryotic cells include, but are not limited to, bacteria. Bacteria that can be used in the methods described herein are, for example, gram positive bacteria, gram negative bacteria, lactic acid bacteria, pathogenic bacteria, filamentous bacteria, methanotrophic bacteria, etc. It is known in the art that filamentous bacteria (such as Streptomyces sp.) can produce toxins or contaminants during their growth phase, after their lag period. As such, the endogenous auto-fluorescent biological markers presented herewith can help in determining where in the cellular cycle the bacteria are located and, ultimately, their ability to produce a toxin. In another embodiment, the bacteria can be derived from at least one of the following family: family Rhizobiaceae, Bacillaceae, Myxophyceae, Cyanophyceae, Pseudomonodaceae, Athiorhodaceae, Thiobacteriaceae, Spirillaceae, Bacteroidaceae, Corynebacteriaceae, Enterobacteriaceae, Rickettsiaceae, Chlamydiaceae, Mycoplasmataceae, Actinomycetaceae, Streptomycetaceae, Mycobacteriaceae, Myxobacteriaceae, Myxobacteriaceae, Micrococcaceae, Lactobacillaceae, Spirochaetaceae, Treponemataceae. In an embodiment, the bacteria can be infected by one or more bacteriophage (such as those from the family Corticoviridae, Cystoviridae, Inoviridae, Leviviridae, Microviridae, Myoviridae, Podoviridae, Siphoviridae, and/or Tectiviridae). It is understood by those skilled in the art that the methods described herein can be used with other families of bacteria and/or bacteriophages.

In another embodiment, the cells can be eukaryotic in nature and can include yeast cells, molds, plant cells and animal cells. Yeast cultures are particularly important for the production of food and food-related additives as well as the production of vaccines. Yeast are unicellular microorganisms that belong to one of three classes: *Ascomycetes, Basidiomycetes* and *Fungi Imperfecti*. Pathogenic yeast strains, or nonpathogenic mutants thereof and non-pathogenic yeast strains can be used in accordance with the method described herein. Examples of yeast strains include *Saccharomyces, Candida, Cryptococcus, Hansenula, Kluyveromyces, Pichia, Rhodotorula, Schizosaccharomyces* and *Yarrowia*. Examples of yeast species include, but are not limited to, *Saccharomyces cerevisiae, Saccharomyces carlsbergensis, Candida albicans, Candida kefyr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus* var. *lactis, Pichia pastoris, Rhodotorula rubra, Schizosaccharomyces pombe,* and *Yarrowia lipolytica*. It is understood the invention is not limited to the strain and species listed above and that one of skill in the art can apply the teachings here in any type of yeast or mold. In another embodiment, yeast and mold cells can be infected during or prior to the in vitro culture.

Animal cells (such as primate cells and non-primate cells) are particularly useful in the in vitro production of epitopes for vaccines as well as antibodies for research or therapeutic uses. They can also benefit from the use of the endogenous auto-fluorescent biological markers presented herein to optimize their culture. The animal cells can be, for example, derived from a primary cell culture, a tissue culture and/or an immortalized cell line. The animal cells may also be infected by one or more of the following family of viruses: Adenoviridae, Reoviridae, Papovaviridae, Calciviridae, Picoviridae, Parvoviridae, Herpesviridae, Retroviridae, Togaviridae, Hepadnaviridae, Rhabdoviridae, Paramyxoviridae, Orthomyxoviridae, Coronaviridae, Bunyaviridae, Poxviridae and/or Arenaviridae. The animal cells can also be infected with a bacteria and/or a protozoa (such as those from the genus *Trypanosoma, Toxoplasma, Leishmania, Plasmodium*). The animal cells can also be infected by a yeast or a mold. The animal cells could also be infected by a proteinaceous infective agent such as a prion.

The endogenous auto-fluorescent biological markers can also be useful in the monitoring or detection of microalgea. Microalgae (such as microphytes) constitute the basic foodstuff for numerous aquaculture species, especially filtering bivalves. They provide them with vitamins and polyunsaturated fatty acids, necessary for the growth of the bivalves which are unable to synthesize it themselves. In addition, because the cells grow in aqueous suspension, they have more efficient access to water, $CO_2$, and other nutrients. Microphytes are microscopic algae, typically found in freshwater and marine systems. They are unicellular species which exist individually, or in chains or groups. Depending on the species, their sizes can range from a few micrometers (µm) to a few hundreds of micrometers. Unlike higher plants, microalgae do not have roots, stems and leaves. Microalgae, capable to perform photosynthesis, are important for life on earth; they produce approximately half of the atmospheric oxygen and use simultaneously the greenhouse gas carbon dioxide to grow photoautotrophically. Most of these microalgae species produce unique products like carotenoids, antioxidants, fatty acids, enzymes, polymers, peptides, toxins and sterols.

The monitoring and detection of plant cells with the endogenous auto-fluorescent marker is also contemplated. For example, a number of plants such as *Catharanthus roseus* (vincristine, vinblastine, ajmalicine), *Taxus baccata* (taxol), *Nothapodytes foetida* (camptothecin), and *Artemisia annua* (artemisinin) have been screened for medicinal uses.

Transgenic plant, that can be cultured in vitro, and can be successfully monitored or detected with the endogenous auto-fluorescent biological marker presented herewith. Transgenic plants are produced by genetic engineering to facilitate the expression of specific compounds, generally proteins, which are extracted and purified after in vitro expansion or harvest. These pharmaceuticals include, but are not limited to, vaccines for infectious diseases, antibodies for therapeutic and diagnostic uses as well as other therapeutic proteins. Many drugs derived from natural products have yet to be artificially synthesized in the laboratory and thus supply remains based upon crude plant materials. One alternative to field grown plants is to culture plant cells in vitro under controlled defined parameters, while retaining the biosynthetic capacity to synthesize bioactive compounds. Unlike field grown plants, in vitro-grown plant cell cultures may prove an excellent source of bioactive compounds because these cell cultures do not suffer from diseases, pests and climatic restraints. In vitro applications of plant cell cultures allow isolation of an unlimited supply of biologically active compounds. In vitro methods provide a closely controlled environment for the optimum growth of plant cells in which cells perform biochemical transformation to synthesize bioactive compounds. Medicinal plants such as Sandalwood (*Santalum album* L.), Periwinkle (*Catharanthus roseus*), and Kantikari (*Solanum Xanthocarpum*) are examples plant species whose cells could be cultured in vitro (e.g. bioreactors).

The plant cell culture can also be derived from a commercially available cell line. In an embodiment, the plant cell culture contains viruses or parasites. In another embodiment, the plant cell culture can be derived from a genetically engineered plant, plant cell or plant cell line.

In a further embodiment, the plant cell culture can comprise more than one type of plant cell or more than one genera of plant cell. The plant cell culture can be derived, for example, from the following genera: *Eschscholtzia* (e.g., *californica*), *Juglans, Fragaria, Lotus, Medicago, Onobrychis, Trifolium, Trigonella, Vigna, Citrus, Linum, Geranium, Manihot, Daucus, Arabidopsis* (e.g. *thaliana*), *Brassica, Raphanus, Sinapis, Atropa* (e.g., *solanaceae, belladonna*), *Capsicum, Datura* (e.g., *solanaceae, mete*)), *Hyoscyamus* (e.g., *niger, albus*), *Lycopersicon, Nicotiana, Solanum* (e.g., *Xanthocarpum*), *Petunia, Digitalis* (e.g., *lanata*), *Majorana, Ciahorium, Helianthus, Lactuca, Bromus, Asparagus, Antirrhinum, Heterocaffis, Nemesis, Pelargonium, Panieum, Pennisetum, Ranunculus, Senecio, Salpiglossis, Cucumis, Browaalia, Glycine, Pisum, Phaseolus, Lolium, Zea, Avena, Hordeum, Secale, Triticum, Catharanthus* (e.g., *roseus* G. Don), *Scopolia* (e.g., *solanaceae*), *Duboisia* (e.g., *solanaceae*), *Taxus* (e.g., *baccata*), *Nothapodytes* (e.g., *foetida*), *Artemisia* (e.g., *annua*), *Santalum* (e.g., *album* L.), *Lithospermum* (e.g., *erythrorhizon*), *Sorghum, Aloe* (e.g., *barbadensis*), *Cinchona* (e.g., *ledgeriana*), *Dioscorea* (e.g., *deltoida, composita*), *Glycyrrhiza* (e.g., *glabra*), *Panax* (e.g., *ginseng*), *Papaver* (e.g., *somniferum*), *Rheum* (e.g., *officinale*), *Rouwolfia* (e.g., *serpentina*), *Eucalyptus* (e.g., *globulus*), *Eugenia* (e.g., *caryophyllata*), *Jasminum, Lavandula* (e.g., *angustffolia*), *Mentha* (e.g., *pzerita*), *Pelargonium, Thaumatocoeus* (e.g., *danielli*), and *Vetiver*. Other plant cell cultures derived from other plants can also be used.

In another embodiment, plant cell may be derived from any part of a plant, including shoot vegetative organs/structures (e.g., leaves, stems and tubers), roots, callus, flowers and floral organs structures (e.g., bracts, sepals, petals, stamens, carpels, anthers and ovules), seed (including embryo, endosperm and seed coat) and fruit (the mature ovary), or plant tissue (e.g., vascular tissue, ground tissue, and the like) or particular cells (e.g., guard cells, egg cells, trichomes, and the like), and progeny of the same. The class of plant cells that can be used in the methods described herein is generally as broad as the class of higher and lower plants amenable to cell culturing techniques, including angiosperms (monocotyledonous and dicotyledonous plants), gymnosperms, ferns, microcellular algae and multicellular algae. It includes plant cells of a variety of ploidy levels, including aneuploid, polyploid, diploid, haploid and hemizygous plants.

Plant cells in liquid suspensions offer a unique combination of physical and biological properties that must be accommodated in large-scale bioreactor processes aimed at exploiting their biomass and synthesis of bioactive compounds. Plant cells have rigid cell walls and tend to grow very slowly with doubling times of days rather than hours. Cultured plant cells range from 30-100 µm in diameter and are 10 to 100 times larger than bacterial and fungal cells. They contain vacuoles occupying 95% or more of the cell's volume. Plant cells are sensitive to shear stress and can be destroyed by impeller speeds as low as 28 RPM in a bioreactor. Some advantages of using plant cell suspension cultures for production of biologically active compounds are low raw material costs, capability of post-translational modification of proteins, and diminished risk of mammalian pathogen contamination.

In order to identify the endogenous biological marker, a correlation of the fluorescence of the endogenous biological plant marker with the parameter can be done with any mathematical formulation capable of accurately describing the relationship between the marker and the biological parameter. For example, and as described herein, the estimation of the biological parameter based on the fluorescence of the endogenous auto-fluorescent biological marker with can be done through a linear regression technique. A linear regression that goes through the origin (0,0) could be performed between the fluorescent signal of the parameter and a standard (offline) measure of the same parameter. The slope of this regression (and the y intercept) enables the conversion of the fluorescent signal to the estimated value for the parameter.

In an embodiment, the biological parameter that is determined by the method is the biomass concentration. As used herein, the term "biomass concentration" refers to the grams of dry weight of cells per liter of culture. The dry weight of cells can easily be determined by those skilled in the art by placing a sample containing cells from the culture onto pre-weighted container, removing the culture media, drying the cells, and weighting them. This cell culture parameter is important because it generates information about the amount of cells in the culture. If the biomass increases during time, it is assumed that the cells accumulate and biosynthesize metabolites meaning that they metabolize properly and are in a growth phase. Some specific markers show an excellent correlation with the biomass concentration. In order to determine the biomass concentration, one or more than one of these markers can be used. These marker include, but are not limited to fluorescent signals associated with tryptamine (excitation wavelength between about 220 and 240 nm, emission wavelength between about 342 and 362 nm), flavin adenine dinucleotide or FAD (excitation wavelength between about 421 and 441 nm and emission wavelength between about 525 and 545 nm) and/or riboflavin and FAD (excitation wavelength between about 442 and 462 nm, emission wavelength between about 522 and 542 nm).

Another parameter that can be easily assessed by the endogenous biological markers described herein is the cellular concentration, i.e. the number of cells per L of culture medium. Cellular concentration is routinely determined by those skilled in the art by using routine techniques (hematocytometer, cell counting, FACS, etc.). This cell culture parameter is important because it generates information about the amount of cells in the culture. If the cellular concentration increases during time, it is assumed that the cells accumulate, biosynthesize metabolites meaning that they metabolize properly and are in a growth phase. Some biological markers show a very accurate correlation with the cellular concentration. In order to determine the cellular concentration, one or more than one of these markers can be used. These markers include, but are not limited to fluorescent signals associated with riboflavin (excitation wavelength of the endogenous auto-fluorescent biological marker is between about 358 and 378 nm, emission wavelength of the endogenous auto-fluorescent biological marker is between about 516 and 536 nm) and/or FAD (excitation wavelength of the endogenous auto-fluorescent biological marker is between about 358 and 378 nm, emission wavelength of the endogenous auto-fluorescent biological marker is between about 522 and 542 nm).

A further parameter that can be easily assessed by the methods described herein is the rate of cellular proliferation ($h^{-1}$). The rate of cellular proliferation is used herein as the length of time required for a cell to go through a complete cellular cycle (e.g. from one cell division to the next). The rate of cellular proliferation is also related to the length of time require for a specific cell population to double. This cell culture parameter is important because it generates information about the growth of cells in the culture. If the rate of cellular proliferation remains positive during time, it is assumed that the cells accumulate, biosynthesize metabolites meaning that they metabolize properly and are in a growth phase. Some biological markers show a very accurate correlation with the rate of cellular proliferation. In order to determine the rate of cellular proliferation, one or more than one of these markers can be used. These markers include, but are not limited to, fluorescent signals associated with nicotinamide adenine dinucleotide phosphate or NAD(P)H (excitation wavelength between about 265 and 285 nm, emission wavelength between about 438 and 458 nm or excitation wavelength between about 340 and 360 nm, emission wavelength between about 435 and 455 nm), riboflavin (excitation wavelength between about 265 and 285 nm, emission wavelength between about 520 and 540 nm), adenosine triphosphate or ATP (excitation wavelength between about 290 and 310 nm, emission wavelength between about 390 and 410 nm), FAD (excitation wavelength between about 421 and 441 nm, emission wavelength between about 525 and 545 nm), a combination of riboflavin and FAD (excitation wavelength between about 442 and 462 nm, emission wavelength between about 522 and 542 nm) and/or pyridoxin (excitation wavelength between about 253 and 273 nm, emission wavelength between about 387 and 397 nm). For some markers associated with the rate of cellular proliferation, an excellent correlation can be obtained by shifting the signal over time. For example, today's measured fluorescent value biomarker can confirm yesterday's cell proliferation rate. This lag of information can correspond to approximately one cell cycle and/or one sampling time.

A further parameter that can be easily assessed by the methods described herein is the rate of biomass growth or accumulation ($h^{-1}$). The rate of biomass growth is used herein as the length of time required for a the biomass to double. This cell culture parameter is important because it generates information about the growth of cells in the culture. If the rate of biomass growth remains positive during time, it is assumed that the cells accumulate, biosynthesize metabolites meaning that they metabolize properly and are in a growth phase. Some biological markers show a very accurate correlation with the rate of cellular proliferation. In order to determine the rate of biomass growth or accumulation, one or more than one of these markers can be used. These markers include, but are not limited to fluorescent signals associated with nicotinamide adenine dinucleotide phosphate or NAD(P)H (excitation wavelength between about 265 and 285 nm, emission wavelength between about 438 and 458 nm), pyridoxine (excitation wavelength between about 313 and 333 nm, emission wavelength between about 384 and 404 nm) and/or sanguinarine (excitation wavelength between about 346 and 366 nm, emission wavelength between about 588 and 608 nm).

Because the markers that have been identified herewith all show an excellent correlation with the growth phase of the cell culture, the present application also provide a method of determining if a cell culture is in a growth phase. In a nutshell, the method comprises determining if the fluorescent signal associated with one of the markers described herein is higher than a control fluorescent signal. If it is the case, then the cells of the culture are believed to be in an active growth phase. The control fluorescent signal is a signal that is not associated with a growth phase of a cell culture, e.g. such as the one associated with the initial lag phase of the culture or the plateau phase that can be observed after a growth phase. This method is particularly advantageous for the optimization of cell culture because, if this method indicates that the cells are not in a growth phase, culture conditions can be modulated (change in nutrients, pH, temperature, etc.) in order that the cells return to a growth phase. In this particular embodiment, the various markers described herein can be used either alone or in combination.

Examples provided herewith show results that were obtained with the culture of plant cells, animal cells, yeast cells, bacteria, microalgae. However, the person skilled in the art will appreciate that those results could also be used in other cell culture systems. In addition, the person skilled in the art will also appreciate that other potential endogenous auto-fluorescent biological markers whose fluorescence is associated with a parameter of a cell culture could be identified in other cell culture system and could also be used in the methods described herein.

The present invention will be more readily understood by referring to the following examples which are given to illustrate the invention rather than to limit its scope.

EXAMPLE I

Determination of Endogenous Biological Markers

Calibration of the spectrophotometer. For each marker tested, a 500 pM aqueous solution was prepared with pure chemicals. Each sample of candidate marker was scanned in 3D ($\lambda_{excitation}$, $\lambda_{emission}$, Relative Fluorescent Unit or RFU) using the microplate reader SAFIRE$^2$ (Tecan) spectrophotometer with excitation and emission wavelengths starting from 50 nm under the theoretical wavelengths of the candidate marker (i.e. excitation and emission wavelengths associated to the peak from the literature) to 50 nm over the theoretical wavelengths. If the reading of the signal is over, the reading gain was adjusted or the original solution was diluted until a clear signal was obtained. This enabled the identification of the excitation and emission wavelength corresponding to the maximal amplitude reading for each peak of the candidate marker.

Optical imprint of the biological marker. The solutions of the markers tested were also scanned in 3D ($\lambda_{excitation}$; $\lambda_{mission}$, Relative Fluorescence Unit or RFU) with a Saphire$^2$ (Tecan) spectrophotometer at the appropriate gain for excitation (e.g. 130), excitation wavelengths from 230 to 750 nm with a minimal step and emission wavelengths from 230 to 750 nm with a minimal step. This 3D scan is also called the optical imprint of the candidate marker. The parameters for the spectrophotometer were the following: bandwidth 5 nm, number of repetition per measurements 5, integration time 41 µs, lag time 0 µs, Z position 11019 µm.

Cell culture. In order to prepare the B5 medium, 500 mL water was poured in a graduated cylinder and stirred. Then, sequentially, 15 mL of a B5 macro-nutrients solution, 1.5 mL of a $CaCl_2$ (1 M), 1.5 mL of B5 micro-nutrients solution, 1.5 mL of EDTA-Fe solution (100 mM), 1.5 mL of B5 vitamins, 0.3 mL of a 2,4-D solution (4.4 mM), 0.15 mL of a kinetin solution (4.65 mM) and 45 g of sucrose were added to the stirring water. The volume of the solution was adjusted to 1 L with water and the solution was stirred to obtain the dissolution of the chemicals. The pH of the solution was then adjusted to 5.5 using a 1M KOH solution. The solution was then sterilized (autoclaved 15 min, 121° C. and 15 psig) for use in the cell culture. In order to prepare the cells, seeds of *Eschscholtzia californica* (Richters inc, #S4720) were sterilized (2 min in EtOH 70%; 15 min in the bleach product JAVEX™; washed twice using sterile water; placed on 2 wet papers within the plastic paraffin film PARAFILM™ sealed sterile Petri dish). Callus were then induced by transferring the germs issued from seeds on solid B5 medium supplemented with 2 g/L of the gelling agent PHYTAGEL™. Callus were maintained and transferred to fresh solid B5 medium every 1 to 3 months depending on growth. The cell line was initiated by transferring the callus cells into liquid B5 medium in a shake flask. Every 14 days, a 30 mL of a two-week old cell culture was added to 60 mL of fresh medium. The cells were cultured for 14 days under constant agitation (120 RPM) at 25° C. Aliquots were taken at various intervals.

Determination of the offline biomass accumulation and biomass accumulation rate. An empty centrifugal tube and a foil paper were first weighted independently. A 2.5 mL aliquot of well mixed cell suspension was taken from the culture and placed into a centrifugal tube using a sterile pipette. The centrifugal tube containing the cell suspension was then weighted. The sample was transferred into a syringe and filtered using a 0.45 µm nitrocellulose filter. The retentate (the cells) was transferred onto the weighted foil paper and was dried in an oven at 80° C. overnight. The foil paper was then weighted. The biomass concentration was obtained by dividing the dry biomass weight (foil and cell weight after oven minus foil weight) by the sample weight (centrifugal tube with sample weight minus centrifugal tube weight). The biomass accumulation rate was obtained for two consecutive samples by the evaluation of:

$$[\ln(b_2/b_1)/(t_2-t_1)]$$

where $b_1$ and $b_2$ are the biomass accumualtion of the first and second samples while $t_1$ and $t_2$ are the sampling time of these samples.

Determination of the offline cell concentration and cellular proliferation rate. A 0.5 mL sample of a well mixed cell suspension was retrieved under sterile conditions and placed in a microcentrifuge tube. Then, 1 mL of an enzymatic solution (citrate buffer (200 mM, pH 4.5) supplemented with sucrose (60 g/L), cellulase (10 U/mL, SIGMA-ALDRICH®, Saint-Louis, Mo., United States of America, C1184), hemicellulase (0.03 U/mL, SIGMA-ALDRICH®. H2125) and pectinase (0.2 U/mL, SIGMA-ALDRICH®. P5146) was added to the microcentrifuge tube. The microcentrifuge tube was placed horizontally on an orbital shaker (120 RPM) for 1 h. The suspension was aspirated three times using a 1 mL micropipette or a cut disposable tip. The microcentrifuge tube was placed horizontally on an orbital shaker (120 RPM) for 30 min. The suspension was aspirated three times using a 1 mL micropipette or a cut disposable tip. To a 50 µL sample of the suspension, 200 µL of a Carbol fushin solution was added (Kao KN (1982) Staining methods for protoplasts and cells. In: Wetter L R, Constabel F (eds) Plant tissue culture methods, 2nd edn. National Research Council of Canada, Saskatoon, Canada, pp 67-71). The suspension was then transferred onto an hemacytometer (Hausser Scientific. 3720) for cell counting under normal light conditions using a microscope. The cell concentration was obtained by dividing the number of cells by the counting chamber volume while taking dilutions into account. The cell proliferation rate was obtained for two consecutive samples by the evaluation of:

$$[\ln(c_2/c_1)/(t_2-t_1)]$$

where $c_1$ and $c_2$ are the cell concentration of the first and second samples while $t_1$ and $t_2$ are the sampling time of these samples.

Analysis of fluorescent parameters of samples cell culture. Raw samples of 200 µL were transferred into an opaque black spectrophotometric plate. Raw samples were also filtered (using a 0.45 mM filter) and 150 mL of the filtered samples were also transferred into the opaque black spectrophotometric plate. The retentate was resuspended in 8.25% saline solution and transferred into the opaque black spectrophotometric plate. 2D and 3D scans of the raw samples, filtered samples and resuspended rententate were performed as indicated above. The 3D scan enabled the determination of RFU for each ($\lambda_{excitation}$, $\lambda_{emission}$) couples. For the retentate value, the RFU amplitude was corrected for the increase in cellular population that occurred during culture. In order to do so, the fluorescent retentate value obtained previously has been corrected with the ratio of the actual biomass concentration/initial biomass concentration.

Determination of RFU amplitude. The RFU amplitude of the raw sample, the filtrate and the resuspended retentate has been obtained by direct measurement using a spectrophotometer. A corrected value has been calculated from the retentate value so as to be representative of the signal amplitude that would result from a reading of the cells fluorescence at the actual cell concentration within the original culture. In order to do so, the raw RFU data of the retentate is multiplied by the ratio of the actual biomass concentration within the original culture/biomass concentration of suspended cells for fluorescence reading with the spectrophotometer. The corrected RFU amplitude is representative of the increase in cellular population occurring during culture.

Determination of the markers. Four spectrophotometric profiles as a function of time for the "raw" sample, the filtered sample, the resuspended retentate and the fresh culture medium were obtained for every cell culture samples. These profiles were compared with specific cell culture parameters (e.g. biomass concentration, cellular proliferation, cellular concentration, biomass accumulation rate, cellular proliferation rate, by-product accumulation, nutrient consumption, etc.). The markers that showed significant relationship with specific cell culture parameters are shown in table 1.

TABLE 1

Nomenclature of useful markers for the monitoring of plant cell culture

| Signal used ($\lambda_{Ex}/\lambda_{Em}$) Molecule | Physiological parameter | | | |
|---|---|---|---|---|
| | Biomass concentration | Cellular concentration | Cellular proliferation | Biomass growth rate |
| Markers from Suspension (untreated) | | | | |
| 230/352 Tryptamine | B1 | | | |
| 275/448 NAD(P)H | | | | TP1$_{-1td}$* |
| 275/530 Riboflavin | | | | TP2$_{-1td}$ |
| 300/400 ATP | | | | TP3$_{-1td}$ |
| 350/445 NAD(P)H | | | | TP4$_{-1td}$ |
| 368/526 Riboflavin | | C1 | | |
| 368/532 FAD | | C2 | | |
| 431/535 FAD | B2 | | | TP5 |
| 452/532 Riboflavin/FAD | B3 | | | TP6 |
| 263/397 Pyridoxin | | | | TP7 |
| Markers from Filtrate | | | | |
| 431/535 FAD | | C3 | | |
| 452/532 Riboflavin/FAD | | C4 | | |
| 263/397 Pyridoxin | | | | TP8 |
| Markers from Retentate (resuspended) | | | | |
| 275/448 NAD(P)H | | | TC1 | |
| 323/394 Pyridoxin | | | TC2 | |
| 356/598 Sanguinarine | | | TC3 | |

TABLE 1-continued

Nomenclature of useful markers for the monitoring of plant cell culture

| Signal used ($\lambda_{Ex}/\lambda_{Em}$) Molecule | Physiological parameter | | | |
|---|---|---|---|---|
| | Biomass concentration | Cellular concentration | Cellular proliferation | Biomass growth rate |
| Other Markers | | | | |
| 263/334 Histidine/phenylalanine | | | | |
| 275/349 Tryptamine | | | | |
| 275/358 Tryptophan | | | | |

EXAMPLE II

Figure 1B:
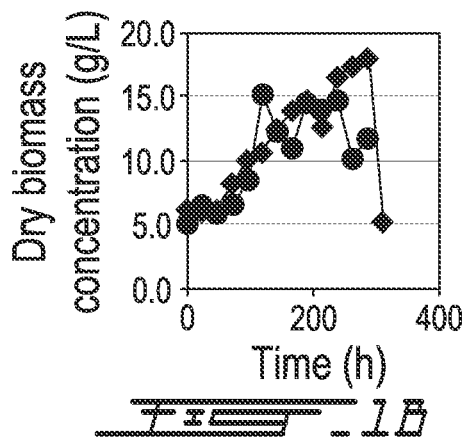
Figure 1C:
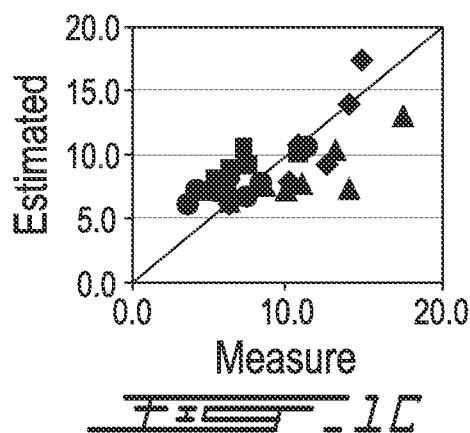
Figure 1D:
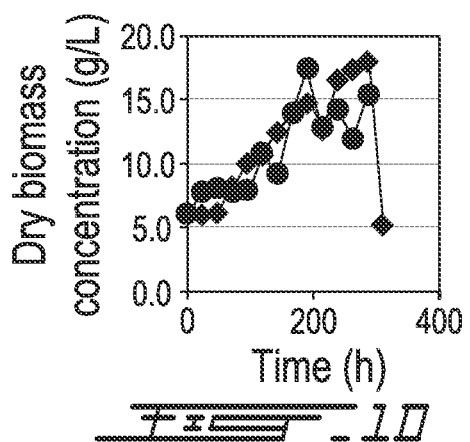
Figure 1E:
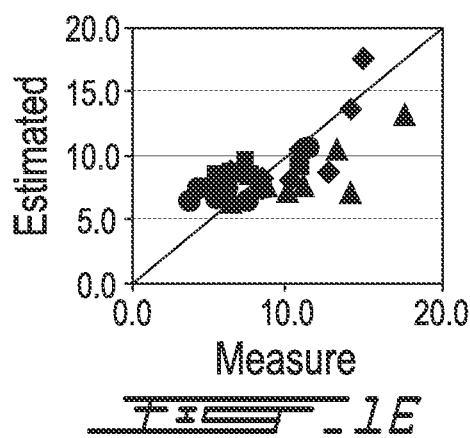
Figure 1F:
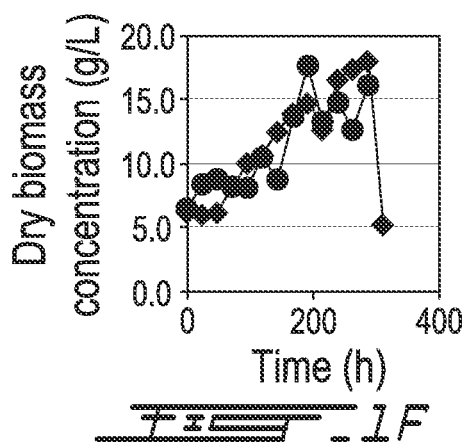

Corrolation of the Endogenous Auto-Fluorescent Biological Marker With Various Biological Parameters Biomass concentration. Three fluorescent signals associated with specific biological markers have been identified as being representative of the biomass concentration: tryptamine ($\lambda_{excitation}$ 230, $\lambda_{emission}$ 352), FAD ($\lambda_{excitation}$ 431, $\lambda_{emission}$ 535) and riboflavin and FAD ($\lambda_{excitation}$ 452, $\lambda_{emission}$ 532). As shown in FIG. 1, the three markers can be used to estimate accurately the biomass concentration. They can also be used to estimate the biomass concentration as a function of time. Further, all three markers correlate with a growth phase of the cell culture.

Figure 2A:
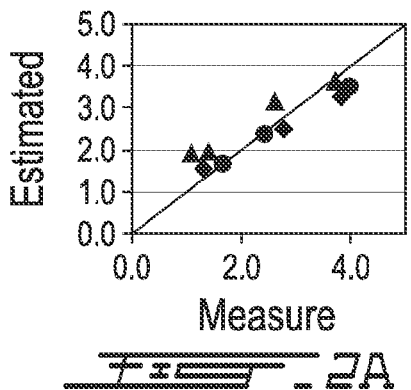
FIG. 2A to 2H illustrate the estimated cellular concentration ($10^9$ cells/L) based on the fluorescence value obtained for different markers and the offline measures of the cellular concentration obtained with traditional techniques. In A, C, E and G the estimated cellular concentration based on the fluorescence value of different markers is plotted against the offline measure of the cellular concentration. The results of three different independent experiment ($\diamond$ experiment 1, $\circ$ experiment 2, $\Delta$ experiment 3) are shown. In B, D, F and H representative results of a single experiment that determined the cellular concentration in function of the length of the culture (in hours) is shown both for the estimated cellular concentration based on the fluorescence value of different markers ($\circ$) and the offline measures ($\diamond$). Results obtained with a riboflavin associated fluorescent signal ($\lambda_{excitation}$ 368 nm, $\lambda_{emission}$ 532 nm) as a marker from the suspension are shown in A and B. Results obtained with a FAD from the suspension are shown in C and D. Results obtained with another FAD associated fluorescent signal ($\lambda_{excitation}$ 431 nm, $\lambda_{emission}$ 535 nm) as a marker from the filtrate are shown in E and F. Results obtained with a riboflavin/FAD associated fluorescent signal ($\lambda_{excitation}$ 452 nm, $\lambda_{emission}$ 532 nm) as a marker from the filtrate are shown in G and H.
Figure 2B:
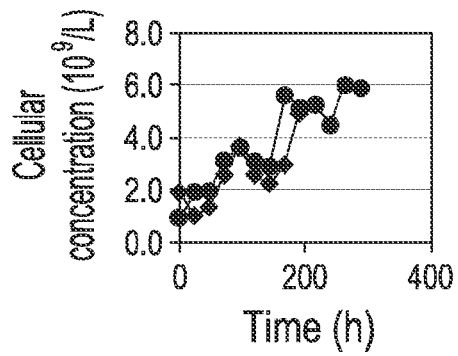
Figure 2C:
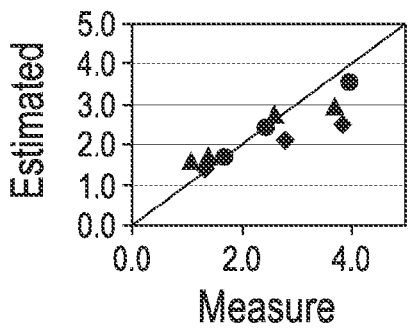
Figure 2D:
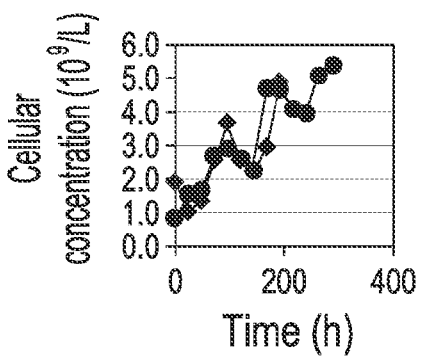
Figure 2E:
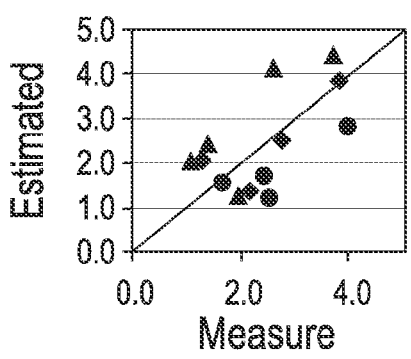
Figure 2F:
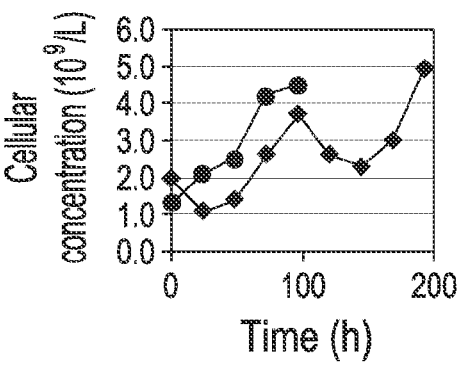
Figure 2G:
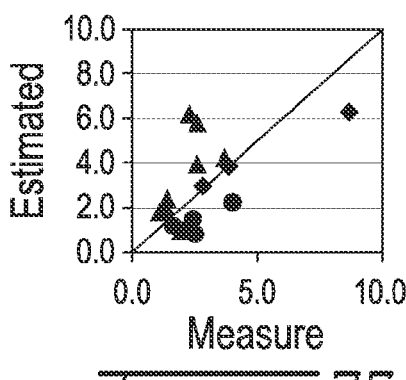
Figure 2H:
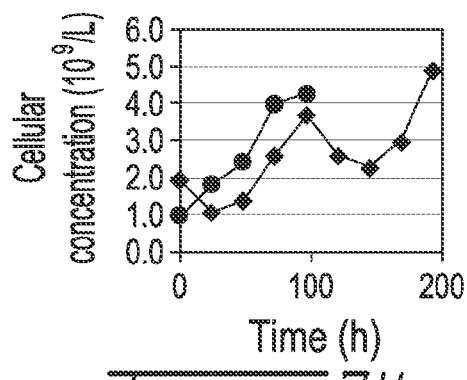

Cellular concentration. Four fluorescent signals associated with specific biological markers have been identified as being representative of the cellular concentration: FAD from the suspension ($\lambda_{xcitation}$ 368, $\lambda_{emission}$ 526), riboflavin from the suspension ($\lambda_{excitation}$ 368, $\lambda_{emission}$ 532), FAD from the filtrate ($\lambda_{excitation}$ 431, $\lambda_{emission}$ 535) and combination riboflavin and FAD from the filtrate ($\lambda_{excitation}$ 452, $\lambda_{emission}$ 532). As shown in FIG. 2, the two markers can be used to estimate accurately the cellular concentration. They can also be used to estimate the cellular concentration as a function of time. Further, both markers correlate with a growth phase of the cell culture.

Figure 3M:
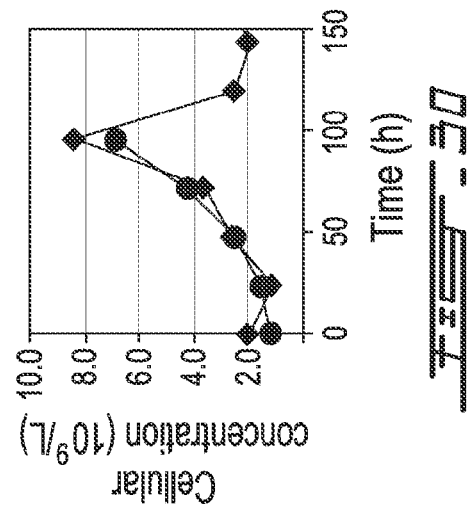
FIG. 3A to 3X illustrate the estimated cellular proliferation rate ($h^{-1}$) and the estimated cellular concentration ($10^9$ cells/L) based on the fluorescence value obtained for height different markers and the offline measures of the same parameters. In A, D, G, J, M, P, S and V the estimated cellular proliferation rate based on the fluorescence value of different markers is plotted against the offline measure of the cellular proliferation rate. The results of three different independent experiment ($\diamond$ experiment 1, $\circ$ experiment 2, $\Delta$ experiment 3) are shown. In B, E, H, K, N, Q, T and W representative results of a single experiment that determined the rate of cellular proliferation as a function of the length of the culture (in hours) is shown for both the estimated rate of cellular proliferation based on the fluorescence value of different markers ($\circ$) and the offline measures ($\diamond$). In C, F, I, L, O, R, U and X representative results of a single experiment that determined the cellular concentration as a function of the length of the culture (in hours) is shown for both the estimated cellular concentration based on the fluorescence value of different markers ($\circ$) and the offline measures ($\diamond$). Results obtained with a NAD(P)H associated fluorescent signal ($\lambda_{excitation}$ 275 nm, $\lambda_{emission}$ 448 nm) as a marker from the suspension are shown in A, B and C. Results obtained with a riboflavine associated fluorescent signal ($\lambda_{excitation}$ 275 nm, $\lambda_{emission}$ 530 nm) as a marker from the suspension are shown in D, E and F. Results obtained with an ATP associated fluorescent signal ($\lambda_{excitation}$ 300 nm, $\lambda_{emission}$ 400 nm) as a marker from the suspension are shown in G, H and I. Results obtained with another NAD(P)H associated fluorescent signal ($\lambda_{excitation}$ 350 nm, $\lambda_{emission}$ 445 nm) as a marker from the suspension are shown in J, K and L. Results obtained with a FAD associated fluorescent signal ($\lambda_{excitation}$ 431 nm, $\lambda_{emission}$ 535 nm) as a marker from the suspension are shown in M, N and O. Results obtained with a riboflavin and marker from the suspension are shown in P, Q and R. Results obtained with a pyridoxine associated fluorescent signal ($\lambda_{excitation}$ 263 nm, $\lambda_{emission}$ 397 nm) as a marker from the suspension are shown in S, T and U. Results obtained with a pyridoxine associated fluorescent signal ($\lambda_{excitation}$ 263 nm, $\lambda_{emission}$ 397 nm) as a marker from the filtrate are shown in V, W and X.
Figure 3P:
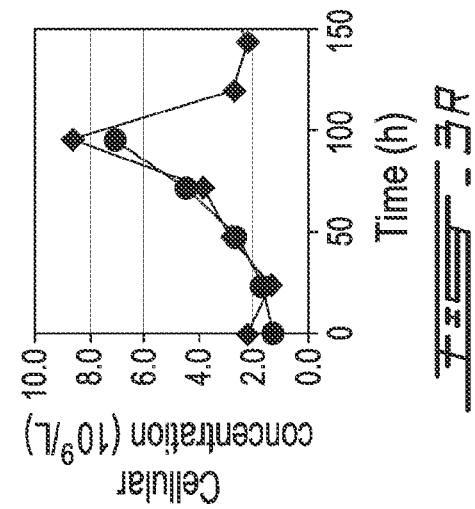
Figure 3N:
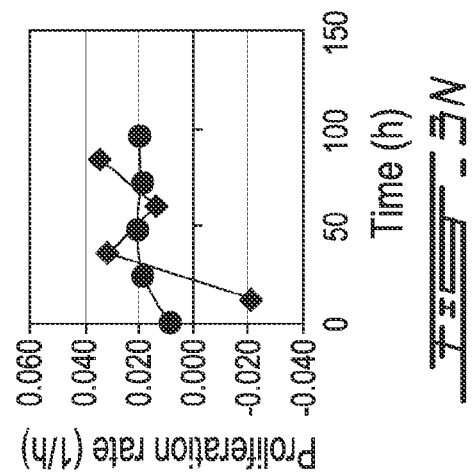
Figure 3Q:
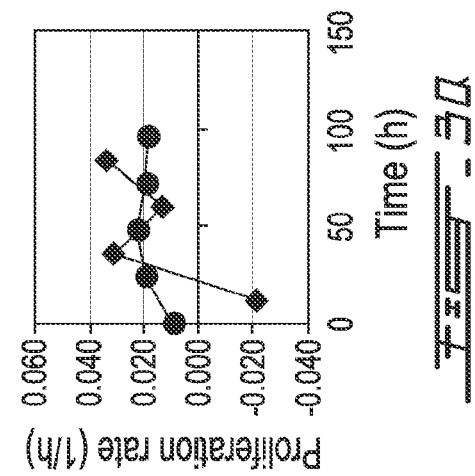
Figure 3O:
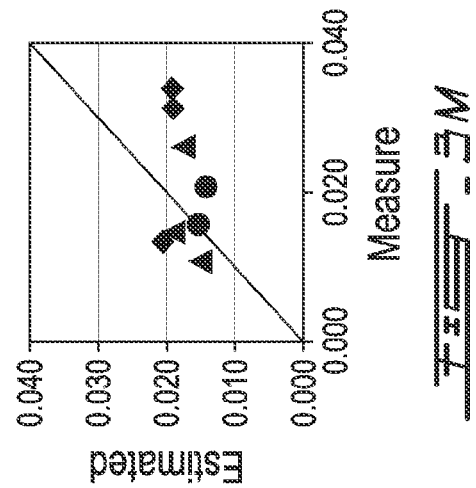
Figure 3R:
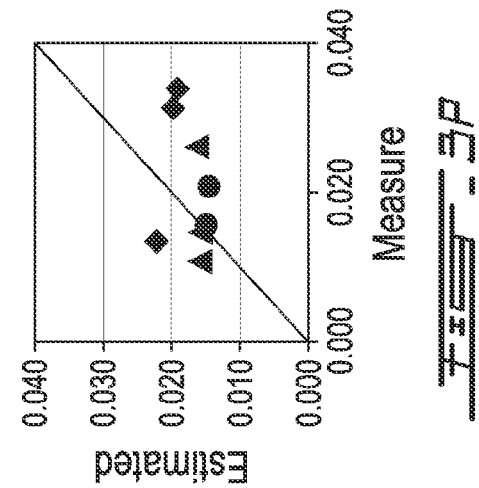

Cellular proliferation. Four fluorescent signals associated with specific biological markers have been identified as being representative of the rate of cellular proliferation: NAD(P)H from the suspension ($\lambda_{excitation}$ 275, $\lambda_{emission}$ 448), riboflavin from the suspension ($\lambda_{excitation}$ 275, $\lambda_{emission}$ 530), ATP from the suspension ($\lambda_{excitation}$ 300, $\lambda_{emission}$ 400) and NAD(P)H from the suspension ($\lambda_{excitation}$ 350, $\lambda_{emission}$ 445). However, the estimated values generated for these four markers show a lag of about a cell cycle with respect to the offline values. As such, the results presented in FIG. 3, for these four markers, have been adjusted to take this effect into account. Four additional fluorescent signals associated with specific biological markers have been identified as being directly linked to the rate of cellular proliferation: FAD from the suspension ($\lambda_{excitation}$ 431, $\lambda_{emission}$ 535), riboflavin and FAD from the suspension ($\lambda_{excitation}$ 452, $\lambda_{emission}$ 532), pyridoxine from the suspension ($\lambda_{excitation}$ 263, $\lambda_{emission}$ 397) and pyridoxine from the retentate ($\lambda_{excitation}$ 263, $\lambda_{emission}$ 397). Contrary to the four markers identified above, these four biological markers do not show a lag period between the results obtained and the actual rate of cellular proliferation. All markers of this example correlate with a growth phase of the cell culture.

Rate of biomass growth. Three fluorescent signals associated with specific biological markers have been identified as being representative of the rate of biomass growth:

NAD(P)H from the retentate ($\lambda_{excitation}$ 275, $\lambda_{emission}$ 448), pyridoxine from the retentate ($\lambda_{excitation}$ 323, $\lambda_{emission}$ 394) and sanguinarine from the retentate ($\lambda_{excitation}$ 356, $\lambda_{emission}$ 598). As shown in FIG. 4, the four markers can be used to estimate accurately the rate of biomass growth. They can also be used to estimate the rate of biomass growth as a function of time.

EXAMPLE III

Use of the Endogenous Biological Markers in Other Biological Systems

*Arabidopsis thaliana*. In order to prepare the MS medium, 500 mL water was poured in a graduated cylinder and stirred. Then, sequentially, 6.45 g of MS salts, 0.885 g of MES, 45 g of sucrose, 1.5 mL of B5 vitamins, 0.3 mL of 2,4-D solution (4.4 mM) were added to the stirring water. The volume of the solution was adjusted to 1 L with water and the solution was stirred to obtain the dissolution of the chemicals. The pH of the solution was the adjusted to 5.7 using a 1M KOH solution. The solution was then sterilized (autoclaved 15 min, 121° C. and 15 psig) for use in the cell culture. Every 7 days, a 15 mL of a two-week old cell culture was added to 30 mL of fresh medium. The cells were cultured for 7 days under constant agitation (120 RPM) at 25° C. Aliquots were taken at various intervals. Fluorescent readings were performed on the cell suspensions only. The determination of fluorescence as well as the determination of offline parameters have been performed according to the methodology set forth in Example I.

*Eschscholtzia californica*. The cells were cultured as presented in Example I. Fluorescent readings were performed on the cell suspensions, filtered samples and resuspended rententate. The determination of fluorescence as well as the determination of offline parameters have been performed according to the methodology set forth in Example I.

*Nannochloropsis* sp. 65 ml of 14 days old microalgae culture were added to 135 ml of sterile f/2 medium. The cells were cultured for 10 days under constant illumination (2000-3000 lux) at 20° C. Aliquots were taken at various intervals. Fluorescent readings were performed on the cell suspensions only. The determination of fluorescence have been performed according to the methodology set forth in Example I. The separation of biomass from the medium has been performed by centrifugation (3200 rpm, 10 minutes). Cell concentration was calculated from suspension directly transferred on an hemacytometer without any prior treatment.

*Saccharomyces cereviciae*. The culture medium was prepared by adding 600 g of malt syrup and 250 g of dextrose to 7 liters of water. The solution was then sterilized (autoclaved 15 min, 121° C. and 15 psig) for use in the cell culture. To initiate cultures, 0.3 mL of a one-week old yeast culture was added to 225 mL of fresh medium. The cells were cultured for 5 days under constant agitation (120 RPM) at 25° C. Aliquots were taken at various intervals. Fluorescent readings were performed on the cell suspensions only. The determination of fluorescence have been performed according to the methodology set forth in Example I. The separation of biomass from the medium has been performed by centrifugation (3200 rpm, 10 minutes). Cell concentration was calculated from suspension directly transferred on an hemacytometer without any prior treatment.

*Streptomyces scabies*. This soil bacterium was cultured in a minimal starch medium (MSM) consisting of 0.5% (w/v) starch 0.5 g l-1 asparagine, 0.5 g/l $K_2HPO_4$, 0.2 g/l $MgSO_4$ and 5 mg/l $FeSO_4$ $7H_2O$. Culture media (50 ml per flask) were sterilized by autoclaving (30 min at 121° C. and 19 psig). $10^8$ bacterial spores were used to inoculate flasks after cooling. Bacterial suspensions were then grown at 30° C. under shaking (250 rpm). Aliquots were taken at various intervals. Fluorescent readings were performed on the cell suspensions only. The determination of fluorescence as well as the determination of biomass concentration have been performed according to the methodology set forth in Example I. Cellular concentration was not measured.

Raji cells. Culture medium was prepared under sterile conditions by adding 40 ml of deactivated (30 min, 56° C.) Cosmic calf serum and 5 ml of Pen/strep/Iglu to 500 ml of RPMI medium base. To initiate cultures, 2 mL of a three-days old suspension were added to 100 mL of fresh medium. The cells were cultured for 6 days under constant $CO_2$ (5%) at 37° C. Aliquots were taken at various intervals. For every aliquot, the cells were filtered out of the culture medium and resuspended in PBS. Fluorescent readings were performed on the cell suspension, filtered samples and resuspended rententate. The determination of fluorescence have been performed according to the methodology set forth in Example I. The separation of biomass from the medium has been performed by centrifugation (1200 rpm, 5 minutes). Cell concentration was calculated from suspension directly transferred on an hemacytometer without any prior treatment.

For each endogenous biological marker/offline parameter, the regression coefficient was calculated and presented in Tables 2 to 5.

In Table 2, results concerning the biomass concentration are presented. It is shown therein that three endogenous biological markers (tryptamine ($\lambda_{excitation}$ 230, $\lambda_{emission}$ 352), FAD ($\lambda_{excitation}$ 431, $\lambda_{emission}$ 535) and a combination of riboflavin and FAD ($\lambda_{excitation}$ 452, $\lambda_{emission}$ 532)) are associated with the biomass concentration in all the biological system examined. These results are consistent with the results obtained in Example II.

In Table 3, results concerning the cellular concentration are presented. It is shown therein that four endogenous biological markers (riboflavin ($\lambda_{excitation}$ 368, $\lambda_{emission}$ 526), FAD ($\lambda_{excitation}$ 368, $\lambda_{emission}$ 532), FAD ($\lambda_{excitation}$ 431 $\lambda_{emission}$ 535) and a combination of riboflavin and FAD ($\lambda_{excitation}$ 452, $\lambda_{emission}$ 532)) are associated with the cellular concentration in all the biological system examined. These results are consistent with the results obtained in Example II.

In Table 4, results concerning the rate of cellular proliferation are presented. In Table 5, results concerning the rate of cellular proliferation are presented. With a shifting of the singal over time as indicated in Example I. It is shown therein that seven endogenous biological markers (pyroxidin ($\lambda_{excitation}$ 263, $\lambda_{emission}$ 397), NAD(P)H ($\lambda_{excitation}$ 275, $\lambda_{emission}$ 448), riboflavin ($\lambda_{excitation}$ 275 $\lambda_{emission}$ 530), ATP ($\lambda_{excitation}$ 300 $\lambda_{emission}$ 400), NAD(P)H ($\lambda_{excitation}$ 350, $\lambda_{emission}$ 445), FAD ($\lambda_{excitation}$ 431 $\lambda_{emission}$ 535) and a combination of riboflavin and FAD ($\lambda_{excitation}$ 452, $\lambda_{emission}$ 532)) are associated with the rate in cellular proliferation in all the biological systems examined. These results are consistent with the results obtained in Example II.

TABLE 2

Regression coefficient results between the fluorescent readings of various endogenous auto-fluorescent biological markers and the biomass concentration. The first column indicates the excitation and emission wavelength. Columns 2 to 7 list the results obtained for the various types of cells (AT = *Arabidopsis thaliana.*, EC = *Eschscholtzia californica*, SC = *Saccharomyces cerevisiae*, NS = *Nannochloropsis* sp., SS =, R = Raji). mean(abs) = mean regression coefficient for all cellular systems analysed, min = minimal regression coefficient, max = maximal regression coefficient, m = number of sample analysed, n = number of assays performed, mn = total number of coordinates.

| Excit/Emiss | AT | EC | SC | NS | SS | R | mean(abs) | min | max |
|---|---|---|---|---|---|---|---|---|---|
| '230 nm/352 nm' | 0.54 | 0.66 | 0.51 | 0.77 | 0.97 | 0.90 | 0.73 | 0.51 | 0.97 |
| '263 nm/334 nm' | 0.68 | 0.06 | 0.83 | 0.03 | 0.88 | 0.40 | 0.48 | 0.03 | 0.88 |
| '263 nm/397 nm' | 0.68 | 0.12 | 0.53 | 0.87 | 0.77 | 0.93 | 0.65 | 0.12 | 0.93 |
| '275 nm/349 nm' | 0.63 | 0.05 | 0.72 | 0.79 | 0.92 | 0.98 | 0.68 | 0.05 | 0.98 |
| '275 nm/358 nm' | 0.67 | 0.11 | 0.69 | 0.83 | 0.93 | 0.97 | 0.70 | 0.11 | 0.97 |
| '275 nm/448 nm' | 0.85 | 0.15 | 0.80 | 0.93 | 0.77 | 0.95 | 0.74 | 0.15 | 0.95 |
| '275 nm/530 nm' | 0.22 | 0.22 | 0.77 | 0.88 | 0.71 | 0.84 | 0.60 | 0.22 | 0.88 |
| '300 nm/400 nm' | 0.83 | 0.06 | 0.51 | 0.85 | 0.76 | 0.98 | 0.67 | 0.06 | 0.98 |
| '323 nm/394 nm' | 0.03 | 0.19 | 0.01 | 0.78 | 0.63 | 0.80 | 0.41 | 0.01 | 0.80 |
| '350 nm/445 nm' | 0.12 | 0.03 | 0.78 | 0.95 | 0.77 | 0.99 | 0.61 | 0.03 | 0.99 |
| '356 nm/598 nm' | 0.58 | 0.22 | 0.90 | 0.86 | 0.58 | 0.00 | 0.52 | 0.22 | 0.90 |
| '368 nm/526 nm' | 0.76 | 0.28 | 0.75 | 0.95 | 0.73 | 0.84 | 0.72 | 0.28 | 0.95 |
| '368 nm/532 nm' | 0.79 | 0.32 | 0.85 | 0.97 | 0.77 | 0.39 | 0.68 | 0.32 | 0.97 |
| '431 nm/535 nm' | 0.88 | 0.79 | 0.89 | 0.97 | 0.92 | 0.47 | 0.82 | 0.79 | 0.97 |
| '452 nm/532 nm' | 0.76 | 0.63 | 0.88 | 0.96 | 0.90 | 0.42 | 0.76 | 0.63 | 0.96 |
| m | 11 | 5 | 4 | 9 | 5 | 5 | | | |
| n | 4 | 2 | 2 | 3 | 5 | 2 | mn = 124 | | |

TABLE 3

Regression coefficient results between the fluorescent readings of various endogenous auto-fluorescent biological markers and the cellular concentration. The first column indicates the excitation and emission wavelength. Columns 2 to 7 list the results obtained for the various types of cells (AT = *Arabidopsis thaliana.*, EC = *Eschscholtzia californica*, SC = *Saccharomyces cerevisiae*, NS = *Nannochloropsis* sp., SS =, R = Raji). mean(abs) = mean regression coefficient for all cellular systems analysed, min = minimal regression coefficient, max = maximal regression coefficient, m = number of sample analysed, n = number of assays performed, mn = total number of coordinates.

| Excit/Emiss | AT | EC | SC | NS | SS | R | mean(abs) | min | max |
|---|---|---|---|---|---|---|---|---|---|
| '230 nm/352 nm' | 0.19 | 0.01 | 0.39 | 0.65 | ND | 0.86 | 0.42 | 0.01 | 0.86 |
| '263 nm/334 nm' | 0.30 | 0.36 | 0.83 | 0.02 | ND | 0.37 | 0.38 | 0.02 | 0.83 |
| '263 nm/397 nm' | 0.27 | 0.45 | 0.80 | 0.94 | ND | 0.91 | 0.67 | 0.27 | 0.94 |
| '275 nm/349 nm' | 0.33 | 0.45 | 0.84 | 0.90 | ND | 0.98 | 0.70 | 0.33 | 0.98 |
| '275 nm/358 nm' | 0.31 | 0.38 | 0.62 | 0.90 | ND | 0.97 | 0.64 | 0.31 | 0.97 |
| '275 nm/448 nm' | 0.32 | 0.43 | 0.97 | 0.90 | ND | 0.93 | 0.71 | 0.32 | 0.97 |
| '275 nm/530 nm' | 0.35 | 0.34 | 0.99 | 0.89 | ND | 0.80 | 0.67 | 0.34 | 0.99 |
| '300 nm/400 nm' | 0.46 | 0.49 | 0.89 | 0.82 | ND | 0.98 | 0.73 | 0.46 | 0.98 |
| '323 nm/394 nm' | 0.01 | 0.55 | 0.00 | 0.73 | ND | 0.74 | 0.41 | 0.00 | 0.74 |
| '350 nm/445 nm' | 0.04 | 0.59 | 0.99 | 0.85 | ND | 1.00 | 0.69 | 0.04 | 1.00 |
| '356 nm/598 nm' | 0.06 | 0.09 | 0.93 | 0.64 | ND | 0.00 | 0.35 | 0.06 | 0.93 |
| '368 nm/526 nm' | 0.46 | 0.25 | 0.97 | 0.75 | ND | 0.88 | 0.66 | 0.25 | 0.97 |
| '368 nm/532 nm' | 0.41 | 0.23 | 0.96 | 0.86 | ND | 0.43 | 0.58 | 0.23 | 0.96 |
| '431 nm/535 nm' | 0.37 | 0.12 | 0.89 | 0.77 | ND | 0.49 | 0.53 | 0.12 | 0.89 |
| '452 nm/532 nm' | 0.47 | 0.12 | 0.89 | 0.81 | ND | 0.50 | 0.56 | 0.12 | 0.89 |
| m | 11 | 5 | 4 | 9 | 0 | 5 | | | |
| n | 4 | 2 | 2 | 3 | 0 | 2 | mn = 99 | | |

TABLE 4

Regression coefficient results between the fluorescent readings of various endogenous auto-fluorescent biological markers and the rate of cellular proliferation. The first column indicates the excitation and emission wavelength. Columns 2 to 7 list the results obtained for the various types of cells (AT = *Arabidopsis thaliana.*, EC = *Eschscholtzia californica*, SC = *Saccharomyces cerevisiae*, NS = *Nannochloropsis* sp., SS =, R = Raji). mean(abs) = mean regression coefficient for all cellular systems analysed, min = minimal regression coefficient, max = maximal regression coefficient, m = number of sample analysed, n = number of assays performed, mn = total number of coordinates.

| Excit/Emiss | AT | EC | SC | NS | SS | R | mean(abs) | min | max |
|---|---|---|---|---|---|---|---|---|---|
| '230 nm/352 nm' | 0.29 | 0.02 | 0.42 | 0.29 | ND | 0.05 | 0.22 | 0.02 | 0.42 |
| '263 nm/334 nm' | 0.10 | 0.17 | 0.79 | 0.02 | ND | 0.31 | 0.28 | 0.02 | 0.79 |
| '263 nm/397 nm' | 0.04 | 0.06 | 0.63 | 0.39 | ND | 0.10 | 0.24 | 0.04 | 0.63 |
| '275 nm/349 nm' | 0.05 | 0.03 | 0.69 | 0.32 | ND | 0.36 | 0.29 | 0.03 | 0.69 |
| '275 nm/358 nm' | 0.08 | 0.03 | 0.62 | 0.34 | ND | 0.30 | 0.27 | 0.03 | 0.62 |
| '275 nm/448 nm' | 0.07 | 0.00 | 0.86 | 0.52 | ND | 0.12 | 0.31 | 0.00 | 0.86 |
| '275 nm/530 nm' | 0.21 | 0.10 | 0.82 | 0.71 | ND | 0.00 | 0.37 | 0.10 | 0.82 |
| '300 nm/400 nm' | 0.09 | 0.07 | 0.59 | 0.32 | ND | 0.34 | 0.28 | 0.07 | 0.59 |
| '323 nm/394 nm' | 0.15 | 0.44 | 0.00 | 0.22 | ND | 0.01 | 0.16 | 0.00 | 0.44 |
| '350 nm/445 nm' | 0.19 | 0.06 | 0.83 | 0.53 | ND | 0.73 | 0.47 | 0.06 | 0.83 |
| '356 nm/598 nm' | 0.03 | 0.05 | 0.93 | 0.77 | ND | 0.95 | 0.55 | 0.03 | 0.95 |
| '368 nm/526 nm' | 0.11 | 0.06 | 0.81 | 0.67 | ND | 0.01 | 0.33 | 0.06 | 0.81 |
| '368 nm/532 nm' | 0.20 | 0.10 | 0.89 | 0.58 | ND | 0.99 | 0.55 | 0.10 | 0.99 |
| '431 nm/535 nm' | 0.13 | 0.12 | 0.94 | 0.52 | ND | 0.83 | 0.51 | 0.12 | 0.94 |
| '452 nm/532 nm' | 0.06 | 0.57 | 0.94 | 0.50 | ND | 0.32 | 0.48 | 0.06 | 0.94 |
| m | 10 | 4 | 3 | 8 | 0 | 4 | | | |
| n | 4 | 2 | 2 | 3 | 0 | 2 | mn = 86 | | |

TABLE 5

Regression coefficient results between the fluorescent readings of endogenous auto-fluorescent biological markers and the rate of cellular proliferation that were adjusted by shifting the signal one sampling period backward over time. The first column shows the excitation and emission wavelength. Columns 2 to 7 list the results obtained for the various types of cells (AT = *Arabidopsis thaliana.*, EC = *Eschscholtzia californica*, SC = *Saccharomyces cerevisiae*, NS = *Nannochloropsis* sp., SS =, R = Raji). mean(abs) = mean regression coefficient for all cellular systems analysed, min = minimal regression coefficient, max = maximal regression coefficient, m = number of sample analysed, n = number of assays, mn = total number of coordinates.

| Excit/Emiss | AT | EC | SC | NS | SS | R | mean(abs) | min | max |
|---|---|---|---|---|---|---|---|---|---|
| '230 nm/352 nm' | 0.23 | 0.57 | 0.78 | 0.56 | ND | ND | 0.54 | 0.23 | 0.78 |
| '263 nm/334 nm' | 0.46 | 0.83 | 0.99 | 0.14 | ND | ND | 0.61 | 0.14 | 0.99 |
| '263 nm/397 nm' | 0.52 | 0.98 | 1.00 | 0.84 | ND | ND | 0.84 | 0.52 | 1.00 |
| '275 nm/349 nm' | 0.38 | 0.97 | 0.91 | 0.75 | ND | ND | 0.76 | 0.38 | 0.97 |
| '275 nm/358 nm' | 0.43 | 0.92 | 0.94 | 0.77 | ND | ND | 0.77 | 0.43 | 0.94 |
| '275 nm/448 nm' | 0.40 | 0.83 | 1.00 | 0.84 | ND | ND | 0.77 | 0.40 | 1.00 |
| '275 nm/530 nm' | 0.01 | 0.93 | 1.00 | 0.99 | ND | ND | 0.73 | 0.01 | 1.00 |
| '300 nm/400 nm' | 0.38 | 0.98 | 0.98 | 0.69 | ND | ND | 0.76 | 0.38 | 0.98 |
| '323 nm/394 nm' | 0.31 | 0.32 | 0.87 | 0.59 | ND | ND | 0.52 | 0.31 | 0.87 |
| '350 nm/445 nm' | 0.26 | 0.99 | 1.00 | 0.88 | ND | ND | 0.78 | 0.26 | 1.00 |
| '356 nm/598 nm' | 0.25 | 0.55 | 0.99 | 0.87 | ND | ND | 0.66 | 0.25 | 0.99 |
| '368 nm/526 nm' | 0.14 | 0.92 | 1.00 | 0.94 | ND | ND | 0.75 | 0.14 | 1.00 |
| '368 nm/532 nm' | 0.09 | 0.90 | 1.00 | 0.84 | ND | ND | 0.71 | 0.09 | 1.00 |
| '431 nm/535 nm' | 0.27 | 0.00 | 0.97 | 0.84 | ND | ND | 0.52 | 0.00 | 0.97 |
| '452 nm/532 nm' | 0.08 | 0.24 | 0.96 | 0.83 | ND | ND | 0.53 | 0.08 | 0.96 |
| m | 10 | 4 | 3 | 8 | 0 | 4 | | | |
| n | 4 | 2 | 2 | 3 | 0 | 2 | mn = 86 | | |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method of determining if the value of a biological parameter of a cell culture in a liquid changes as a function of time, said method comprising:
   (a) irradiating the cell culture or a sample thereof with a light source emitting a specific excitation wavelength to generate a fluorescent signal from an endogenous auto-fluorescent biological marker;
(b) quantifying, at a specific emission wavelength, the fluorescent signal associated with the endogenous auto-fluorescent biological marker to obtain a fluorescent value;
(c) determining if the fluorescent value of step (b) changes as a function of time in the cell culture; and
(d) determining the biological parameter of the cell culture based on the fluorescent value in real time, wherein a modulation in the fluorescent value indicates a modulation in the value of the biological parameter characterizing the value of the biological parameter (i) as changing as a function of time when the fluorescent value is determined, in step (c), to change as a function of time and (ii) as remaining the same as a function of time when the fluorescent value is determined, in step (c) to remain the same;
wherein the biological parameter is a rate of cellular proliferation ($h^{-1}$) and the endogenous auto-fluorescent biological marker is associated with:
pyroxidine and has the specific excitation wavelength between about 253 and 273 nm and the specific emission wavelength between about 387 and 407 nm;
NAD(P)H and has the specific excitation wavelength between about 265 and 285 nm and the specific emission wavelength between about 438 and 458 nm;
NAD(P)H and has the specific excitation wavelength between about 340 and 360 nm and the specific emission wavelength between about 435 and 455 nm;
riboflavin and has the specific excitation wavelength between about 265 and 285 nm and the specific emission wavelength between about 520 and 540 nm;
ATP and has the specific excitation wavelength between about 290 and 310 nm and the specific emission wavelength between about 390 and 410 nm;
FAD and has the specific excitation wavelength between about 421 and 441 nm and the specific emission wavelength between about 525 and 545 nm; and/or
a combination of riboflavin and FAD and has the specific excitation wavelength between about 442 and 462 nm and the specific emission wavelength between about 522 and 542 nm.

2. The method of claim 1, wherein the sample of the cell culture is filtered prior to step (a) to generate a filtrate and a retentate.

3. The method of claim 1, wherein step (d) further comprises shifting the fluorescent signal over time to determine the biological parameter.

4. The method of claim 1, wherein the endogenous auto-fluorescent marker is associated with pyroxidine and has the specific excitation wavelength between about 253 and 273 nm and the specific emission wavelength between about 387 and 407 nm.

5. The method of claim 1, wherein the endogenous auto-fluorescent marker is associated with NAD(P)H and has the specific excitation wavelength between about 265 and 285 nm and the specific emission wavelength between about 438 and 458 nm.

6. The method of claim 1, wherein the endogenous auto-fluorescent marker is associated with NAD(P)H and has the specific excitation wavelength between about 340 and 360 nm and the specific emission wavelength between about 435 and 455 nm.

7. The method of claim 1, wherein the endogenous auto-fluorescent marker is associated with riboflavin and has the specific excitation wavelength between about 265 and 285 nm and the specific emission wavelength between about 520 and 540 nm.

8. The method of claim 1, wherein the endogenous auto-fluorescent marker is associated with ATP and has the specific excitation wavelength between about 290 and 310 nm and the specific emission wavelength between about 390 and 410 nm.

9. The method of claim 1, wherein the endogenous auto-fluorescent marker is associated with FAD and has the specific excitation wavelength between about 421 and 441 nm and the specific emission wavelength between about 525 and 545 nm.

10. The method of claim 1, wherein the endogenous auto-fluorescent marker is associated with a combination of riboflavin and FAD and has the specific excitation wavelength between about 442 and 462 nm and the specific emission wavelength between about 522 and 542 nm.

* * * * *